(12) United States Patent
Jedwab et al.

(10) Patent No.: US 11,006,892 B2
(45) Date of Patent: May 18, 2021

(54) TECHNIQUE FOR DETERMINING A SWALLOWING DEFICIENCY

(71) Applicant: NESTEC S.A., Vevey (CH)

(72) Inventors: Michael Jedwab, Lausanne (CH); Adam Burbidge, Arzier (CH)

(73) Assignee: Societe des Produits Neslte S.A., Vevey (CH)

( * ) Notice: Subject to any disclaimer, the term of this patent is extended or adjusted under 35 U.S.C. 154(b) by 198 days.

(21) Appl. No.: 15/302,859

(22) PCT Filed: Mar. 19, 2015

(86) PCT No.: PCT/EP2015/055740
§ 371 (c)(1),
(2) Date: Oct. 7, 2016

(87) PCT Pub. No.: WO2015/154960
PCT Pub. Date: Oct. 15, 2015

(65) Prior Publication Data
US 2017/0027495 A1  Feb. 2, 2017

(30) Foreign Application Priority Data

Apr. 9, 2014 (EP) .................................... 14164002

(51) Int. Cl.
*A61B 5/00* (2006.01)
*G16H 50/20* (2018.01)
(Continued)

(52) U.S. Cl.
CPC ............ *A61B 5/4205* (2013.01); *A61B 1/273* (2013.01); *A61B 1/2733* (2013.01); *A61B 5/0022* (2013.01); *A61B 5/0071* (2013.01); *A61B 5/1455* (2013.01); *A61B 5/4233* (2013.01); *A61B 5/687* (2013.01); *A61B 5/6822* (2013.01); *A61B 5/6867* (2013.01);
(Continued)

(58) Field of Classification Search
CPC ..... A61B 5/687; A61B 5/4205; A61B 5/4233; A61B 5/6822; A61B 5/7267; A61B 1/273; A61B 1/2733
See application file for complete search history.

(56) References Cited

U.S. PATENT DOCUMENTS

| 5,976,084 A | 11/1999 | Tymchuck |
| 2005/0283096 A1 | 12/2005 | Chau et al. |

(Continued)

FOREIGN PATENT DOCUMENTS

| CN | 101005799 A | 7/2007 |
| CN | 102348407 A | 2/2012 |

(Continued)

OTHER PUBLICATIONS

Gupta, et al., Surface EMG Measurements at the Throat during Dry and Wet Swallowing, 1996, Dysphagia 11: p. 173-179.*

(Continued)

*Primary Examiner* — Daniel L Cerioni
*Assistant Examiner* — Raymond P Dulman
(74) *Attorney, Agent, or Firm* — K&L Gates LLP

(57) ABSTRACT

The invention relates to a device for assessing the characteristics of the swallowing process in a subject a sensor that is capable of detecting vibrations of the throat during swallowing.

15 Claims, 6 Drawing Sheets

(51) Int. Cl.
*A61B 1/273* (2006.01)
*A61B 5/1455* (2006.01)
*A61B 7/00* (2006.01)
*A61B 5/11* (2006.01)

(52) U.S. Cl.
CPC .......... *A61B 5/7225* (2013.01); *A61B 5/7267* (2013.01); *A61B 5/7275* (2013.01); *A61B 7/008* (2013.01); *G16H 50/20* (2018.01); *A61B 5/1107* (2013.01); *A61B 2562/0219* (2013.01)

(56) References Cited

U.S. PATENT DOCUMENTS

| | | | | |
|---|---|---|---|---|
| 2007/0224126 | A1* | 9/2007 | Dufresne | A61B 5/00 424/9.2 |
| 2008/0306373 | A1* | 12/2008 | Kandori | A61B 5/1126 600/407 |
| 2009/0030346 | A1* | 1/2009 | Kojima | A61B 5/11 600/590 |
| 2009/0227908 | A1* | 9/2009 | Chau | A61B 5/11 600/595 |
| 2011/0160615 | A1* | 6/2011 | Matsumura | A61B 5/4205 600/587 |
| 2011/0276312 | A1* | 11/2011 | Shalon | A61B 5/11 702/187 |
| 2012/0258195 | A1 | 10/2012 | Sliwinski | |
| 2013/0204617 | A1* | 8/2013 | Kuo | H04R 3/002 704/233 |
| 2013/0296662 | A1* | 11/2013 | Omari | A61B 5/037 600/301 |
| 2013/0310661 | A1 | 11/2013 | Jedwab et al. | |
| 2014/0004045 | A1* | 1/2014 | Mendenhall | A61K 47/00 424/9.1 |
| 2014/0306827 | A1* | 10/2014 | Inoue | A01K 29/005 340/573.3 |

FOREIGN PATENT DOCUMENTS

| | | |
|---|---|---|
| CN | 103338700 A | 10/2013 |
| WO | 2013086615 | 6/2013 |

OTHER PUBLICATIONS

Ramalhosa, et al., Mead production: Tradition versus modernity, Dec. 2011, Advances in food nutrition and research, p. 110.*
Hayashi, et al., Relationship Between Rice-Gruel Properties and Swallowing Motion, 2002, The Journal of the Japanese Society of Dysphagia Rehabilitation, 6 (2), p. 73-81.*
Keren, et al., Solid Swallowing versus Water Swallowing: Manometric Study of Dysphagia, Digestive Diseases and Sciences, Apr. 1992, vol. 37, No. 4, p. 603-608. (Year: 1992).*
Malagelada et al. "Dysphagia" World Gastroenterology Organisation, 2007, 14 pages.
Chinese Office Action for corresponding responding Chinese Application No. 2015800184633, dated Nov. 2, 2018; (9 pages).
Guo, "Scientific and Statistical Method of Clinical Medicine", Edition 1, Nov. 1992, pp. 137-138.
Li, "Speech Therapy", Edition 1, Jan. 2014, pp. 194-199.
China Patent Office Action Received for Application No. 201580018463.3, dated Dec. 29, 2020, 24 pages.

* cited by examiner

TECHNIQUE FOR DETERMINING A SWALLOWING DEFICIENCY

CROSS REFERENCE TO RELATED APPLICATIONS

The present application is a National Stage of International Application No. PCT/EP2015/055740, filed on Mar. 19, 2015, which claims priority to European Patent Application No. 14164002.9, filed Apr. 9, 2014, the entire contents of which are being incorporated herein by reference.

The present invention relates generally to a technique for determining a swallowing deficiency, wherein the technique may be used as a support for screening and/or assessing dysphagia, in particular oropharyngeal dysphagia.

Dysphagia refers to the symptom of difficulty in swallowing which may include swallowing disorder such as abnormalities within the oral, pharyngeal and esophageal phases of swallowing. For example, oropharyngeal dysphagia may manifest itself by difficulties controlling food in the mouth, the inability to control food or saliva in the mouth, difficulties initiating a swallow, coughing, choking, frequent pneumonia, etc.

Dysphagia may result from neurological impairment including, amongst others, cerebrovascular accidents, brain injuries, Parkinson's disease, stroke and multiple sclerosis. A diagnosis of dysphagia may seek establishing the location of the perceived swallow problem (e.g., oropharyngeal vs. esophageal dysphagia). Generally, an accurate history covering a manifold of different diagnostic elements (including screening) is to be established for a reliable diagnosis.

Neurological and neuromuscular disturbances that produce oropharyngeal dysphagia can rarely be corrected through pharmacological or surgical therapy. Therefore the management of complications is of paramount importance, wherein the identification of risks for aspiration is a key element when considering treatment options. In this regard, modifying food consistency can be an important approach. For example, fluids and soft foods can be thickened. Subjects with swallowing difficulties may find thin liquids cause coughing, spluttering or choking. A thickened consistency enables a subject to swallow safely, e.g. makes it less likely that an individual with dysphagia will aspirate while drinking.

Various thickening agents or thickeners are available for the dietary management of dysphagia. These substances provide for an increase of viscosity of a solution or liquid/solid mixture. Agents are available which aim at not substantially modifying further properties of the food, while other agents for example add or modify taste. Thickeners may be used for providing food or beverage with a consistency as appropriate for any individual patient. For instance, in terms of increasing viscosity or rheology, thickeners may be used to provide a nectar-type, a honey-type or pudding-type consistency as desired for an individual.

Various medical guidelines are available for diagnosing dysphagia. For example, the "World Gastroenterology Organisation Practice Guidelines" retrievable in the Web and regarding Dysphagia describe a plurality of examinations, from which a subset may be performed as required for fully diagnosing an individual, starting with unspecific examinations and continuing to more specific examinations to eventually arrive at an accurate diagnosis of dysphagia which may include that an appropriate thickener consistency is identified by the examination personnel.

The timed water-swallow test is a basic and cost-efficient screening test which may be applied to complement evidence obtained by physical examination. The subject drinks 150 milliliter of water from a glass as quickly as possible. Time taken and number of swallows are recorded. Based on these data, the speed of swallowing and the average volume per swallow can be calculated. The test is believed to have a high predictive sensitivity for identifying the presence of dysphagia. The water-swallow test may be complemented by a food test, wherein a small amount of pudding is placed on the dorsum of the tongue.

U.S. Pat. No. 7,749,177 B2 (U.S. '177 hereinafter) describes an apparatus for detecting aspiration. The apparatus may be employed as a screening tool and/or assessment tool for measuring the risk of dysphagia (presence or absence of swallowing deficiency, in terms of swallowing safety and/or swallowing efficiency) and may for example be employed when swallowing activity is examined in the course of a water swallow test. An accelerometer detects swallowing activity and provides an electronic signal to a computing device which operates to extract features from that signal to classify the signal and accordingly the swallowing activity. Exemplary activities to be detected and/or classified may include swallows, aspirations, and movement/vocal artifacts.

Swallowing accelerometry is related to cervical auscultation, but uses computing technology such as digital signal processing and/or artificial intelligence as discrimination tools rather than trained medical personnel. For example, neural networks may be employed for classifying normal and "dysphagic" swallows. Accordingly, an apparatus for detecting swallowing activity may include an accelerometer that is positioned on the throat of a patient. A computing device may be connected to the accelerometer. The computing device may be operable to receive signals from the accelerometer, to detect swallowing activity from such signals, and to report on those activities by presenting corresponding output on a display.

For detecting swallowing activities, specific aspects may be extracted from the recorded signals, for example stationarity, normality and/or dispersion ratio of the signal may be analyzed. The signal may then be classified based on the extracted features. The classification may be performed using a neural network which classifies swallowing events as either healthy swallows or aspirations ("unhealthy swallows"). An output is generated corresponding to the classification. For example, where a particular event was classified as a swallow, a textual message "SWALLOW" may be displayed, whereas if the event was classified as an aspiration then a message "ASPIRATION" may be displayed.

Having established the presence (or absence) of risk of dysphagia, more specific examinations may subsequently be performed to analyze a swallowing deficiency in more detail and/or establish a specific therapy. More specific examinations may often comprise examinations monitoring an individual's swallowing activity.

With FEES ("Fiberendoscopic Evaluation of Swallowing"), food intake via the pharyngeal zone is monitored using a flexible endoscopic instrument intubated via the nose. Consistencies comprising liquid, paste-like, solid, crumbly are swallowed, and are known in general as "stimuli".

A barium swallow study or videofluoroscopic swallow study may be performed in case oropharyngeal and/or esophagial dysphagia is considered as a cause for swallowing difficulties. Due to fast progression of a swallow, a video is produced via X-ray cinematography or digital spot imaging for later slow motion reproduction. Various contrast meals are used from thin/liquid to solid ("barium cookie")

for simulating intake. A sequence of videos, generally from a lateral perspective, may be produced from X-rays that provide information on bolus transport and safest consistency of bolus. A set of different consistencies may be swallowed including thin, nectar, honey, pudding, puree, regular consistency.

A first examination including, for example, a water swallow test requires few medical tools only and can be performed cost-efficiently anywhere in a medical practice, hospital or at a subject's home. However, such examination delivers unspecific results only, as it merely determines the presence or absence of a swallowing deficiency without allowing further insights into the nature of deficiency and appropriate measures to be taken. Subsequent examinations such as videofluoroscopy are necessary which are costly due to complex medical apparatus required and which may not plainly be available but can be performed only in dedicated medical centers, with attendant irradiation.

There is a need for a technique for determining swallowing difficulties which can be employed, amongst others, as a support for screening or assessing the risk of dysphagia.

There is a need for a medical technique for determination of swallowing difficulties which can be employed not only as a screening tool but as a screening and/or an assessment tool supporting a more specific diagnosis of dysphagia.

There is a need for a non-invasive technique which can be implemented with low costs as compared to currently available tools and avoiding radiation.

There is a need for a technique which can be utilized in general medical practice and hospitals, for example in rehab hospitals.

There is a need for a technique which can be implemented by non-stationary tooling in order to be used, for example, at a subject's home.

One or more of the above needs is satisfied by a kit for determining a swallowing deficiency. The kit is suitable for assessing the characteristics of the swallowing process in a subject, particularly for assessing the risk of aspiration, wherein said risk of aspiration comprises assessing swallowing safety and/or assessing swallowing efficiency and comprises:

at least one device 108 comprising a processing unit 140 and a sensor 104 said sensor 104 adapted to detect externally or internally on a throat 110 of a subject 102 vibrations, and to provide a sensor signal 114 indicative of the detected throat vibrations;
  a thickening agent 106 for thickening a fluid for producing at least one item of foodstuff (118) with a defined texture for intake by the subject;
optionally water 130;
  wherein said processing unit 140 is designed to assess the swallowing characteristics of a subject by processing the sensor signal 114 associated with the intake of a foodstuff item 118 selected from at least two defined foodstuff items differing by their texture, optionally one of the two defined foodstuff items being water.
  and to output a signal 126 representing the result of the determination.

The invention is also directed to corresponding methods and uses.

The sensor can be an accelerometer, an acoustic sensor, or another sensor capable of detecting vibrations of a throat.

The signal that is output by the sensor signal can be binary providing a yes- or no-answer with respect to the risk for aspiration, or wherein the signal that is output by the sensor signal is scored on the Penetration Aspiration Scale (PAS) indicated by the values 1-8, or in the form of another score indicative of the characteristics of the swallowing process.

The texture of the item of the defined foodstuff 118 to be produced with the thickening agent 106 can be different from the texture of water.

The thickening agent 106 can be configured for producing at least a first foodstuff item 118 with a first texture and a second foodstuff item 120 with a second texture, the first texture being different from the second texture.

The thickening agent 106 can be configured for producing different textures by adding different dosages of the thickening agent to the fluid.

The first and second texture can differ by their fluid property said fluid property being selected from the group consisting of density, viscosity, consistency, and rheology of the foodstuff items.

The thickening agent 106 can be configured for producing at least one of a first defined foodstuff item with a texture having a nectar-type viscosity, a second foodstuff item having a honey-type viscosity, and a third foodstuff item having a pudding-type viscosity.

The thickening agent can be provided in form of one or more unit portions 206, the unit portions 206 being adapted for achieving one or more specific textures when combining the thickening agent with the fluid.

The device 108 can comprise at least one of a computing hardware comprising a processing unit, a computer readable medium having computer executable instructions, a computer-executable software, and a link providing access to a remote or local computing facility.

The invention also relates to a replenishment package 202 for replenishment of the kit 100 according to any of the above claims, comprising:
a thickening agent for thickening a fluid for producing at least one item of defined foodstuff for intake by a subject, wherein the thickening agent is provided in form of one or more unit portions 206, the unit portions being adapted for achieving one or more different specific textures when combining the thickening agent with a fluid.

Training of Processing Unit

The invention is also directed to method for training a processing unit 140 for assessing the characteristics of the swallowing process in a subject 102, particularly for assessing the risk of aspiration, wherein said risk of aspiration comprises assessing swallowing safety and/or assessing swallowing efficiency.

During the training phase, the foodstuff 118 must be rendered radiopaque (hereafter "tagged foodstuff") via the addition of barium sulfate for example. The actual doses of foodstuff used are reduced appropriately to compensate for the added viscosity due to the addition of barium. The resulting viscosity closely matches the viscosity obtained when the normal doses of 118 are mixed with water alone. Swallows of the barium stimuli will be simultaneously recorded using accelerometry and VFSS.

According to the present invention, in the method of training the processing unit (140)
said processing unit 140 is supplied with a signal 114 from a sensor 104 capable of detecting throat vibrations,
said sensor 104 adapted to detect externally or internally on a throat 110 of a subject vibrations,
wherein said processing unit after the training is capable of outputting an indication of the characteristics of the swallowing process in a subject, particularly for assessing the risk of aspiration, resulting from the intake of an item of a food stuff 118 with a given texture, wherein said processing unit 140 is capable of accepting from a sensor 104 a sensor signal 114 associated with the intake of an item of tagged foodstuff by a subject, comprising the steps:

a) performing at least once the following steps:
  i) providing to a subject one item of tagged foodstuff for oral intake, said tagged foodstuff item being selected from at least two defined tagged foodstuffs differing by their texture,
  ii) assessing the characteristics of the swallowing process in the subject resulting from the intake of the item of tagged foodstuff by the subject with a reference technique capable of assessing the characteristics of the swallowing process said reference technique being selected from the group consisting of an imaging technique, fiberoptic endoscopic evaluation of swallowing (FEES), fiberoptic endoscopic evaluation of swallowing with sensory testing (FEESST), pulse oximetry or other appropriate techniques.
  iii) using the results of step i) and ii)) for training the processing unit 140; and
b) thereby obtaining a trained processing unit (140).

Steps i)-iii) can be performed for 1-1'000, 400-600, or 500 subjects. Steps i)-iii) can be repeated at least once. For each subject the steps i)-iii) are performed at least once. Each subject is provided with one or a sequence of foodstuff item or items.

The trained processing unit obtained in step iii) is then submitted to steps i)-iii) with a further patient if training occurs with a further patient. Thus, the processing unit undergoes repetitive training with different patients. Thus, the algorithm may evolve as a function of these repeated iterations until the desired sensitivity and specificity target are obtained.

The imaging technique can be video fluoroscopy (VF).

The training in step iii) can comprise determining a sensor signal 114 resulting from the throat vibrations resulting from the intake of the item of tagged foodstuff by the subject 102, and forwarding said sensor signal (114) to the processing unit 140 operated by a computer executable software and thereby providing an assessment of the characteristics of the swallowing process, and wherein said assessment resulting from the sensor signal 114 is correlated with the assessment resulting from the imaging technique of step ii).

Steps i) to iii) can be repeated at least once to improve the correlation between the assessment of the characteristics of the swallowing process of a subject resulting from the sensor signal and the assessment of the characteristics of the swallowing process resulting from the imaging technique, wherein the subject can be the same or different, wherein optionally the different subjects can be 1-1'000 different subjects. Thus the algorithm may evolve as a function of these repeated iterations until the desired sensitivity and specificity target are obtained.

The method can implement a neural network or the method determines parameters of a computer executable software, said executable software running on and instructing the trained processor.

The training phase can comprise
a) providing said trained processing unit
b) performing the method defined in step a) of claim 1 on the trained processing unit on the subjects of a group of subjects said group comprising 10-30, preferably 20, subjects,
c) thereby obtaining a further trained processing unit
d) resubmitting the obtained trained processing unit to steps b)-d) for 1-30, 10-25, 18-22, or 20 times.

Thus the algorithm may evolve as a function of these repeated iterations until the desired sensitivity and specificity target are obtained.

Validation of the Trained Processing Unit

The method can further comprise a step c) wherein the trained unit is validated in a validation phase.

The method can comprise a further step wherein it is validated that the trained processing unit provides the same assessment of the characteristics of the swallowing process of a subject as the reference technique by comparing the indication of a swallowing deficiency output by the reference technique and output by the trained processing unit, and thereby obtaining a trained and validated processing unit. It is to be noted that the algorithm used in the validation phase is fixed as opposed to the iteratively evolving algorithm in the training phase. The algorithm used in the validation phase should therefore be the version that gives the best sensitivity and specificity results.

According to the present invention, in the method of validating the processing unit (140)
said processing unit 140 is supplied with a signal 114 from a sensor 104 capable of detecting throat vibrations, said sensor 104 adapted to detect externally or internally on a throat 110 of a subject vibrations,
wherein said processing unit after the training is capable of outputting an indication of the characteristics of the swallowing process in a subject, particularly for assessing the risk of aspiration, resulting from the intake of an item of a food stuff 118 with a given texture,
wherein said processing unit 140 is capable of accepting from a sensor 104 a sensor signal 114 associated with the intake of an item of tagged foodstuff by a subject, comprising the steps:
performing at least once the following steps:
  i) providing to a subject one item of tagged foodstuff for oral intake, said tagged foodstuff item being selected from at least two defined tagged foodstuffs differing by their texture,
  ii) assessing the characteristics of the swallowing process in the subject resulting from the intake of the item of tagged foodstuff by the subject with a reference technique capable of assessing the characteristics of the swallowing process said reference technique being selected from the group consisting of an imaging technique, fiberoptic endoscopic evaluation of swallowing (FEES), fiberoptic endoscopic evaluation of swallowing with sensory testing (FEESST), pulse oximetry or other appropriate techniques.
  iii) using the results of step i) and ii) for validating processing unit 140.

The obtained trained and optionally validated processing unit is capable of outputting an indication of a swallowing deficiency, wherein said risk of aspiration comprises assessing swallowing safety and/or assessing swallowing efficiency, with a sensitivity of between 50% and 100%, between 60 and 90%, or 80%, and/or wherein the obtained trained and optionally validated processing unit is capable of outputting an indication of a swallowing deficiency, assessing said risk of aspiration comprises assessing swallowing safety and/or assessing swallowing efficiency, with a specificity of between 50% and 100%, between 60 and 90%, or 80%.

Thus, the method is also directed to assessing swallowing safety with a sensitivity of between 50% and 100%, between 60 and 90%, or 80%, and/or wherein the obtained trained and optionally validated processing unit is capable of outputting an indication of a swallowing safety with a specificity of between 50% and 100%, between 60 and 90%, or 80%.

The method can also directed to assessing swallowing efficiency with a sensitivity of between 50% and 100%, between 60 and 90%, or 80%, and/or wherein the obtained trained and optionally validated processing unit is capable of outputting an indication of a swallowing efficiency with a specificity of between 50% and 100%, between 60 and 90%, or 80%. For example, a sensitivity of 80% would mean that on 10 patients that aspirate (as assessed by video fluoroscopy, VFS), the device of the invention will correctly detect 8 of the 10 patient and 2 will be assessed false-negatively. For a specificity of 80%, 10 patients that are assessed as not aspirating by VFS, the device of the invention will detect 8 out of 10, and give false positive assessments for 2 out of 10.

Foodtuff Items

In the method of the invention steps i)-iii) can be performed at least twice with one food stuff item selected from the group consisting of water, a foodstuff item with a texture having a nectar-type viscosity, a foodstuff item having a honey-type viscosity, and a foodstuff item having a pudding-type viscosity; thus associating the performing of each step i) with one specific foodstuff item thereby providing a sequence of foodstuff items that is to be provided to the subject in step a) or the sequence of provided foodstuff items may be arbitrary.

The at least two, three, or four different foodstuff items can be selected from the group consisting of water, a foodstuff item with a texture having a nectar-type viscosity, a foodstuff item having a honey-type viscosity, and a foodstuff item having a pudding-type viscosity are provided in step a) to the subject.

In the sequence of foodstuff items to be provided at least two of the foodstuff items can be the same or different.

The sequence of foodstuff items to be provided to the subject in step a) can be any permutation of the at least two, three, or four different foodstuffs being selected from the group consisting of water, a foodstuff item with a texture having a nectar-type viscosity, a foodstuff item having a honey-type viscosity, and a foodstuff item having a pudding-type viscosity.

Within each sequence of foodstuffs to be provided to the subject none of the foodstuffs might be provided twice.

The sequence can be water, a foodstuff item with a texture having a nectar-type viscosity, a foodstuff item having a honey-type viscosity, and a foodstuff item having a pudding-type viscosity.

One of the at least two foodstuffs (118) of step a) i) in step a) of claim 12 is water.

The invention is also directed to a processing unit (140) obtained by the method described above.

Disclosed is also a device comprising:
a) the trained processing unit of the invention;
b) a sensor 104 adapted to detect externally or internally on a throat of a subject vibrations.

Method

The invention also covers a method for assessing the characteristics of the swallowing in a subject, particularly for assessing the risk of aspiration, comprising the steps:
a) providing to a subject 102 at least one item of foodstuff 118 for oral intake,
b) assessing the characteristics of the swallowing in a subject 102 associated with the intake of the item of foodstuff 118 by the subject with the device of the invention.

This foodstuff item 118 can be selected from at least two defined foodstuff (118, 120) items differing by their texture.

One of the at least two defined foodstuff (118, 130) items can be water.

In the method for assessing the characteristics of the swallowing in a subject steps a) and b) can be repeated with a foodstuff that has a different texture than the previously used item of foodstuff.

In the method for assessing the characteristics of the swallowing in a subject the first provided foodstuff item can be water 130.

The invention also relates to the device of invention for assessing the characteristics of the swallowing in a subject 102, in particular, for assessing the risk of aspiration in a subject.

The device 108 can be used in combination with a thickening agent 106.

In addition, the invention is directed to the use of a thickening agent 106 suitable for providing at least one item of foodstuff 118 for oral intake, said foodstuff item 118 selected from at least two defined foodstuffs (118, 120) differing by their texture for assessing the characteristics of the swallowing process in a subject 102, particularly for determining the risk of aspiration in a subject, with the device of the invention.

Definitions

As used herein, the term "swallow" may be understood as designating a safe passage of foodstuff from the oral cavity, through the hypopharynx and into esophagus. Further, a swallow is normally accompanied by a period of apnea with no entry of foodstuff into the protected airway. In contrast, an "aspiration" may mean the entry of foreign material into the airway during inspiration. The term "swallowing activity" may comprise a swallow or an aspiration or the absence of either.

A "swallowing deficiency" from a physiological view may comprise any deficiency of a swallowing activity with respect to a successful swallowing, i.e. a swallow. A swallowing deficiency does not necessarily lead to an increased risk of aspiration, i.e. the deficient swallowing activity may lead to a swallow, but may take long, may be less efficient in terms of swallowed volume, may be accompanied by peculiarities in parts or portions of the subject's body involved in the swallowing activity, etc. A swallowing deficiency may be reported from the subject, medical or nursing personnel, and/or may be determined by the computer-based tool. For example, the tool may determine presence of a swallowing deficiency while neither the subject nor medical personnel from, e.g., physical inspection would be aware of a deficiency.

A swallowing deficiency can comprise two aspects: Swallowing safety and swallowing efficiency. Each of these aspects can be assessed alone. Swallowing safety relates to the assessment of the risk for aspiration. A low risk for aspiration translates into a high swallowing safety. Swallowing efficiency relates to the degree that an item to be swallowed is swallowed. Thus, a high swallowing efficiency means that a high portion of the item to be swallowed is swallowed.

In general, any part, portion or aspect of a swallowing activity represented in the throat vibrations and in turn represented in the sensor signal as detected by the sensor may be defined as a "swallowing deficiency". Resulting from current or future scientific research, for example, it is assumed that any particular shape, form, occurrence, etc. of a part, portion or aspect of the sensor signal may be predefined as peculiar, i.e. as representing a swallowing deficiency. U.S. '177 provides a detailed discussion including further references on relationships between sensor signal aspects and swallowing deficiencies.

The term "swallowing deficiency" as used herein may therefore designate any part, portion, and/or other aspect such as a statistical or stochastic property of a sensor signal which is predefined to be related to a physiological swallowing deficiency, or which may be predefined in the future according to new scientific findings. Swallowing deficiency comprises swallowing safety (assessment of risk of aspiration) and swallowing efficiency (assessment of amount of residue after swallowing).

The term "foodstuff" as generally used herein may designate any kind of stuff which may be provided for intake by a subject including food and goods regularly and generally used for nutrition purposes, which may include water, and which may include diet food, or any other kind of food prepared for one or more specific aims. The term "foodstuff" may additionally or alternatively comprise stuff for intake for examination or diagnostic purposes, which may include any stuff not recommended or available for regular intake and with specific ingredients such as ingredients providing for radiation (e.g. barium sulfate), coloring, flavor enhancement, artificial sweetening, etc. One foodstuff item is water without any thickening agent (e.g. purified water, tap water).

DETAILED EMBODIMENTS

The sensor may comprise any sensing equipment adapted for sensing throat vibrations. For example, the sensor may comprise an accelerometer. Such devices and their application to measure throat vibrations are well known in the art and these aspects will therefore not be discussed in detail herein.

The sensor signal may comprise an analogue signal, for example an electric signal which represents the detected throat vibrations by variations in voltage, current, and/or other electric properties. Additionally or alternatively, the sensor signal may comprise a digital signal which represents throat vibrations in form of, for example, a bit sequence. According to some embodiments, a signal may be gained in analogue form and will then be converted into a digital signal. Such analogue-to-digital conversion may be performed at the sensor, a device or system comprising the sensor, and/or by a separate A/D-converter.

A data connection between sensor and processing unit may be based on a physical connection such as a wireline connection, for example via a fixedly attached and/or detachable cable. Additionally or alternatively, the data connection may be implemented as a wireless connection such as Bluetooth or Wi-fi. The data connection may be a direct connection and/or may pass through a network such as an intranet or the Internet.

The device may accept the sensor signal in push and/or pull-mode. According to various embodiments, the device may comprise a computing hardware based on, for example, a general and/or dedicated purpose processor such as an ASIC or a DSP. According to various embodiments, the device may be implemented as described in the U.S. '177. According to some embodiments, the device is implemented according to the prescriptions as described in U.S. '177 with further properties as discussed in detail herein.

The device may additionally or alternatively be embodied as a computer readable medium such as a DVD, CD-ROM, a FLASH memory such as an USB stick, etc., wherein the medium represents instructions which can be executed when read into a computing device as one or more software and/or firmware programs.

According to various embodiments, the thickening agent may be provided for thickening one or more of the following fluids: water, tea, coffee, soup, and any other fluidic medium or liquid which may be used within the framework of the invention. The "fluid" to be used may however not only include thin media with a viscosity less, around or close to that of water, but may also include media which have a higher viscosity prior to being combined with the thickening agents. The "fluid" may therefore include any kind of flowable matter, thin fluid, thick fluid, semi-fluidic matter, viscous or pasty matter, etc.

According to some embodiments, the inventive technique may comprise that one fluid only, e.g., water, is envisaged to be thickened by the thickening agent. Replacement of water by tea, coffee, soup, etc. may or may not be envisaged. According to other embodiments, more than one fluid may be envisaged to be thickened by the thickening agent; for example, a first foodstuff item may be produced by thickening a first fluid with the thickening agent, and a second foodstuff item may be produced by thickening a second fluid with the thickening agent, wherein at least one property such as a texture of the first and second fluid differ from each other.

According to various embodiments, a fluid may be intended for intake without being thickened and none, one or more foodstuff items containing that fluid in thickened form may be intended for intake. According to some of these embodiments, water may be used for intake without thickening, e.g. as a first foodstuff item, and water thickened by the thickening agent may be used for intake as a second (and/or third, etc.) foodstuff item.

According to some embodiments, one or more thickening agents may be provided with the kit. The thickening agent or agents presently supposed to be advantageous for implementing the invention may comprise, for example, at least one of xanthan gum, potassium, and cornstarch, wherein one or more of these ingredients may be modified. The skilled artisan is aware of adjuvants, auxiliary and further materials, for example sweetener, etc. which may be added according to the details of any specific environment in which the invention may be applied. The thickening agent or agents may be provided as a powder and/or other solid dosage form, which may, e.g., be water soluble, and/or may be provided as a fluid, e.g. in pasty form. However, a dry or dried form may be preferable for shipping, storage, and/or service life depending on the field of application of the kit.

The thickening agent or agents may be configured to produce, when combined with the fluid, a foodstuff item with a specific or well-defined texture. For example, the thickening agent may be adapted to be stable with regard to its thickening properties over the timescales for shipping and storing the inventive kit until use. The thickening agent may be adapted to have homogeneous thickening properties such that repeating a same application of the agent repeatedly leads to the same results.

According to various embodiments, an item of foodstuff may be understood as designating an entity, unit or bolus of foodstuff which is defined appropriate for examining swallowing difficulties. A foodstuff item may correspond to an average bit or mouthful, but may also correspond to more or less than that. For example, an item of foodstuff may be intended to comprise several bolus or swallows (fluid or solid).

An item of foodstuff, at least when prepared for intake, may generally have homogeneous properties throughout, e.g. for any pair of two subitems formed by subdividing the item in an arbitrary way, the subitems may have the same texture. For example, an item of foodstuff resulting from thickening a fluid with a thickening agent may comprise specific, well-defined and well-detectable properties (fluid property) regarding, e.g., a well-defined consistency, viscosity, and/or rheology, due to dissolving, stirring, mixing, merging, blending, etc.

Homogeneous properties of an item ready for intake do not exclude that an item of foodstuff may be produced as a mixture of two or more different kinds of foodstuff, e.g. different fluids, or a fluid and a solid material, e.g. a powder mixed with water, before being combined with the thickening agent. As an example, an item of foodstuff when ready for intake may comprise a particular kind of solid food such as a powder mixed with a defined amount of water and additionally or alternatively thickened with a defined amount of the thickening agent to achieve a defined texture, e.g. a defined viscosity.

The item when ready for intake may comprise a particular weight, amount of material, and/or volume. For example, an item of foodstuff may comprise 100 milliliter (ml) of water. Another item of foodstuff may comprise 100 ml of water combined with 1.2 gram (g) of thickening agent. Still another foodstuff may comprise 100 ml of water combined with 2.4 g of thickening agent, etc. Another foodstuff item may comprise a solid material, or a plurality of small pieces, crumbs, or lumps, with a defined total weight and/or volume.

The texture of the item or items of foodstuff produced by the fluid and the thickening agent may comprise any of consistency, viscosity, rheology, or a combination thereof, but the term may also be applied to other foodstuff, for example solid foodstuff and may then include properties such as crumbly, brittle, etc.

The term "defined texture" is amongst others intended to indicate that the item of foodstuff can be assigned a specific texture or texture range which is applicable for the item as a whole as well as any part or portion thereof, i.e. a foodstuff item with homogeneous properties can be assigned a single, well-defined value describing, e.g., its viscosity, rheology, etc. The adjective "defined" may also include a reproducible texture such that any foodstuff item made from a fluid and a thickening agent according to the same prescription will have the same texture, which may include in turn that a fluid and a thickening agent are selected as appropriate for reproducible properties.

Apart from texture, at least one of the fluid, the thickening agent and the resulting foodstuff item may comprise flavor, color, and/or any other property which may be contemplated of use for a diagnostic purpose, for example for examining children, dement individuals, etc.

According to various embodiments, the defined texture of at least one item of foodstuff to be produced with the thickening agent is different from the texture of water. For example, the thickening agent may be combined with water to achieve a foodstuff item with nectar-type, honey-type, or pudding-type viscosity.

The thickening agent may be configured for producing at least a first foodstuff item with a first texture and a second foodstuff item with a second texture, the first texture being different from the second texture. For example, one and the same thickening agent may be added to water and/or another fluid with different dosages, to arrive at different textures. Additionally or alternatively, different textures may be achieved with one and the same dosage, for example by using different fluids, different ways of preparing the foodstuff items for intake, e.g., via heating, stirring, etc.

According to various embodiments, one or more thickening agents may be provided with the kit to produce two or more foodstuff items with two or more different textures.

The textures may differ in at least one of viscosity, consistency, rheology, and/or other properties which may be related to examining and/or avoiding swallowing difficulties.

According to various embodiments, textures may be measured in terms of viscosities, for example in units of milliPascal multiplied by seconds "mPa s". According to various embodiments, values of viscosities may be intended to be measured and/or defined for foodstuff items at a shear rate of 50/s and a temperature of 25° C. (Celsius degree) as prescribed, for example, by the NDD (National Dysphagia Diet Task Force). Additionally or alternatively, other prescriptions of other authorities may be applied. As an example, according to other embodiments viscosities may be measured at a shear rate of 30/s, or at still another shear rate.

It may be noted that the NDD was developed for starch-based thickeners. More modern thickeners use xanthan gum for example and the definitions of the NDD may not strictly apply. For example, 1.2 g in a 100 ml of water of a xanthan based thickener may give a Nectar value of about 160 mPa s, 2.4 g in 100 ml of water of a xanthan based thickener may give a Honey value of about 600 mPa s, and 3.6 g in 100 ml of water of a xanthan based thickener may give a Pudding value of about 880 mPa s.

Generally, when considering a set of two or more foodstuff items with differing textures intended for supporting a determination of swallowing difficulties, the textures may fall into different texture ranges, e.g. viscosity ranges. For example, in case of two foodstuff items, a first item may be intended to have a viscosity falling into the range of 50 mPA s to 350 mPa s, while a second item may be intended to have a viscosity falling into a range of more than 350 mPa s to 1750 mPa s.

As another example, in case of three foodstuff items, a first item may be intended to have a viscosity falling into a range of 50 mPa s to 300 mPa s, a second item may be intended to have a viscosity falling into the range of 301 mPA s to 1750 mPa s, while a third item may be intended to have a viscosity falling into the range of more than 1750 mPa s.

A "thin-type" viscosity encompassing the viscosity of water and many other thin fluids such as tea or coffee may be defined to have a viscosity falling into a range of 1 mPa s to 50 mPa s. An item, fluid or general matter having a viscosity falling into a range of 51 mPA s to 350 mPa s may be designated as "nectar-type". An item or other matter having a viscosity falling into the range of 351 mPa s to 1750 mPa s may be designated as "honey-type". An item or other matter having a viscosity falling into the range of 1751 mPa s or above may be designated as "pudding-type". While the above follows a standard classification of bolus consistencies of the NDD, other classifications can be followed and/or contemplated. Various viscosity classifications are known and used in the field. A general classification may define various classes. One class may relate to "thin"/"thin liquid"/"thin-type"/"thin-like" textures, another class may relate to "nectar"/"nectar-type"/"nectar-like" textures, a further class may relate to "honey"/"honey-type"/"honey-like" textures, a still further class may relate to "pudding"/"pudding-type"/"pudding-like" textures.

Other embodiments may comprise more textures and/or items to be tested. Examples for other or additional classes related to flowable matter may comprise "thin honey" or "spoon-thick", wherein the latter may or may not be defined to have a different viscosity range from "pudding". Additionally or alternatively further classes may comprise mash, solid, brittle, crumbly, or still other textures.

According to various embodiments, one or more of the textures intended for examination may be fluid-type or thin. The foodstuff item representing such texture may, for example, be simply water as used in a conventional water-swallow test or other fluid readily available at the examination site. Therefore embodiments of the kit may or may not comprise water, dried tea or coffee powder, etc. for producing corresponding foodstuff items. Generally, if it is intended to perform an examination based on providing a specific number of foodstuff items to the subject, the kit may comprise a fewer number of ingredient articles per examination. Otherwise, if multiple ingredients are required for producing one or more foodstuff items, the kit may comprise a higher number of ingredient articles.

For example, if it is intended to determine or test swallowing difficulties based on two textures, wherein one texture is supposed to be thin-type, e.g., represented by water, the kit may be delivered with thickening agent to produce one foodstuff item having the intended second texture different from the texture of water. As another example, in case it is intended to perform an examination with five textures thin, nectar, honey, pudding, solid, the kit may comprise thickening agent to prepare nectar, honey, and pudding by combining the agent with water or other soluble, while thin may be directly provided by the soluble, and the kit may further comprise at least one solid foodstuff item for the fifth class.

According to various embodiments, the thickening agent may be provided in form of one or more unit portions. For example, the thickening agent may be provided in a kit encapsulated in a plurality of solid or soft boxes, containers, capsules, cells, pads, small jars, which may optionally be packed in one or more blisters, etc., wherein a packaging material may comprise a plastics or synthetic pr other material as appropriate for food and/or medical purposes and the kit being generally intended for testing a plurality of subjects.

The unit portions may be adapted for achieving one or more defined textures when combining the thickening agent with the fluid according to predefined prescriptions. For example, for a given kit containing a plurality of unit portions of thickening agent, a nectar-type foodstuff item may be produced from a first defined amount of water or a similar fluid added with one unit portion of thickening agent, i.e. the content of a package containing one unit portion of thickening agent may be added to a container with a prescribed amount of water. From the same kit, a honey-type foodstuff item may be produced from a second defined amount of water added with two unit portions of thickening agent. A pudding-type foodstuff item may be produced from a third defined amount of water added with three unit portions of thickening agent. The first, second and third amount of water may be same or different.

According to another embodiment, nectar-type, honey-type, and pudding-type items may not be produced from one, two and three unit portions of thickening agent, but two, three, and four unit portions, respectively. Many other packaging approaches for the thickening agent can be contemplated, wherein providing the thickening agent in unit portions (or in other packaged form) may contribute to achieving foodstuff items with a specific defined and reproducible texture, and/or may simplify following hygiene prescriptions, etc.

The kit may comprise at least one measuring receptacle 324 for portioning the thickening agent. For example, the receptacle may be embodied as a measuring spoon for portioning the thickening agent. Additionally or alternatively, a receptacle may be provided for combining the thickening agent with the fluid. For example, a measuring container, jug, graduated cup, glass, etc. can be provided for filling with a desired portion of the thickening agent, a desired amount of fluid, and/or for mixing both. The measuring receptacle or receptacles may contribute to achieving one or more defined and/or specific textures.

While one or more thickening agents are provided with the kit for producing one or more foodstuff items for examination, this does not exclude performing an examination with one or more further foodstuff items without thickening agent being added. For example, one or more foodstuff items may be prepared for intake based on water or other fluid or matter not included in the kit. Additionally or alternatively, the kit may comprise foodstuff items which are ready for intake or to be prepared for intake without adding one or more thickening agents.

Generally, the kit may comprise one or more foodstuff items ready for intake or for preparation prior to intake in dried form. For example, one or more of the items may require mixing with water and/or other solubles as a preparation for intake. A kit comprising dried materials only, including the thickening agent may be especially appropriate for shipping and storing.

The device may or may not comprise a dedicated computing hardware. According to various embodiments, the computing hardware may comprise a computing device such as a general purpose computer, e.g. a personal computer (PC), notebook, tablet, personal digital assistant (PDA), etc. Additionally or alternatively, the computing hardware may comprise a processing unit, a programmable (micro)processor, an application specific integrated circuit (ASIC), a digital signal processor (DSP), one or more of these, or combinations thereof.

Additionally or alternatively, the device may comprise a computer readable medium having computer executable instructions. For example, the medium may be embodied as a removable CD-ROM, DVD or USB stick with software and/or firmware stored thereon. Additionally or alternatively, the device may comprise software which can be executed by a computing device when loaded into a random-access memory (RAM) or read-only memory (ROM). For example, a software or firmware may be provided on an erasable programmable ROM (EPROM) or a similar semi-permanent or permanent storage area of an ASIC, DSP or other specific or general purpose processor.

According to some embodiments, the device may comprise software provided, for example, for download to a computing device via a data connection, e.g. via a computer network such as the Internet, an intranet, etc.

According to various embodiments, the device may comprise a link providing access to a remote computing facility. The link may comprise, for example, one or more of a data link, network link, and web link. The link may provide access to a computing facility which may provide any or part of the computing resources discussed herein for implementing the invention. The computing facilities or resources may for example be provided by a server or multiple serving capabilities reachable via a network.

The link may be accompanied with a password for getting access to the provided facilities or resources. Additionally or alternatively, other data may be provided with the kit, such as a user manual for the tool, prescriptions on how to perform examinations, references to medical guides, etc. In an embodiment the device is able to output result in a format suitable for electronic data patient records, and maybe compatible with a variety of hospital-based Patient Data Management Systems (PDMS).

As outlined above and further discussed elsewhere herein, the term "device" does not necessarily imply that a dedicated computing hardware and/or software is at hand to the practitioner using the invention. For example, the practitioner may be given with the kit a web address or link to be accessed using a general web browser as presented on a display managed by a general purpose computer such as a personal computer, tablet, or other. In such cases, the computing resources required for determining swallowing deficiencies according to the invention are in general located remote from the examination site. Additionally or alternatively, software may be provided for download via the link, for example in the form of an application or applet to be installed on a PC, tablet, etc., to work as a stand-alone application, as a functional extension of a web-browser, etc.

In this respect, the "device" may include a "computing tool", such as a computing hardware; however, according to some embodiments the computing tool may be embodied as a PC, PDA, tablet, etc. at hand of the examiner (local device), while in other cases the computing tool may be embodied on a remote server to be accessed by the examiner (remote device). Combinations of these embodiments can be contemplated, wherein a computing hardware at hand of the examiner or practitioner functions for input/output of data, while calculations are performed remote.

In an embodiment, the device is able to record data readings for a given patient over time and thereby track the progress of the patient. In addition, the proposed therapeutic intervention maybe adapted/personalized as the patients condition evolves (e.g. after stroke)

According to various embodiments, the device may be configured for accepting an input indicative of one or more foodstuff items, at least one foodstuff, one or more textures, and/or a sequence of intake of foodstuff items by the subject. For example, a user may input one or more item indications to enable the device generating associations between one or more sensor signals or portions thereof and an item or a sequence of items swallowed by the measured subject. Additionally or alternatively, a user may indicate textures such as thin, nectar, honey, pudding to the tool.

Additionally or alternatively, a user may indicate a sequence "thin, nectar, honey, pudding", or a sequence "pudding, honey, nectar, thin" to the tool or other sequences. One or more of the indications may be presented by the tool, for example, in a menu, to let the user select one or more of the offered indications.

According to various embodiments, the device may be adapted to calculate based on the sensor signal whether a detected swallowing activity corresponds to a successful swallow, an aspiration of foodstuff, or presence of residues or intermediate.

For swallowing safety, a number can be calculated indicating a successful or unsuccessful swallowing on a continuous scale, wherein the scale may reach, for example, from 0 to 1. Values in a range between 1.0 and 0.7 may, e.g., be defined as safe swallow, while values in the range between 0.3 and 0.0 may be defined as aspiration. Values in the range between 0.7 and 0.3 may be defined as intermediate or unclear. Such intermediate values may for example be interpreted as aspiration for safety reasons and/or may be output with a recommendation for repeating the corresponding intake, etc. It is to be understood that swallowing activity being classified as intermediate by the tool may correspond to slight swallowing difficulties the subject may not be fully aware of and/or which may not easily be noticeable by physical examination (e.g. silent aspiration).

Alternatively, the signal can produce a binary output, providing a yes- or no-answer with respect to the risk for aspiration, or wherein the signal that is output by the sensor signal is scored on the Penetration Aspiration Scale (PAS) indicated by the values 1-8, or in the form of another score indicative of the characteristics of the swallowing process.

For swallowing efficiency, a number can be calculated indicating the degree by which an item to be swallowed is swallowed on a continuous scale, wherein the scale may reach, for example, from 0 to 1. Values in a range between 1.0 and 0.7 may, e.g., be defined as efficient swallow, while values in the range between 0.3 and 0.0 may be defined as inefficient swallow. Values in the range between 0.7 and 0.3 may be defined as intermediate or unclear. Such intermediate values may for example be interpreted as inefficient swallow and/or may be output with a recommendation for repeating the corresponding intake, etc. It is to be understood that swallowing efficiency being classified as intermediate by the tool may correspond to slightly inefficient swallowing the subject may not be fully aware of and/or which may not easily be noticeable by physical examination (e.g. residues).

Alternatively, the device can produce a binary output, meaning a yes or no answer with respect to swallowing efficiency.

According to some embodiments, the device can be configured to calculate an output texture based on the textures of one or more foodstuff item intakes. Such calculations may be output and may be used by the examiner as a support for proceeding with the next intake. Based on such intermediate calculations, for example, a range of safe textures may be examined by a nested interval approach.

The device may provide for an output indicative of a texture which has been determined to not cause swallowing deficiency. Additionally or alternatively, a result can be output for each performed intake. According to some embodiments, a sequence of determination results may be provided, for example for the subject to be tested. The sequence may not only map number of intake to determination result, but may map texture and/or foodstuff item to a determination result. Texture and/or foodstuff, which have been determined to not cause swallowing deficiency, may be presented in highlighted form such as in a different color, flashing, etc. Additionally or alternatively, an intake, texture and/or foodstuff for which a deficiency has been determined may be presented in highlighted format.

A summary can be presented, e.g., at the end of an examination, which may indicate that no deficiencies have been determined, or that deficiencies have been determined. In the latter case, a recommendation can be presented, which may comprise in indication of texture, foodstuff or one or more types of food which can be swallowed safely according to the determination. As an example, a range of viscosities enabling safe swallowing according to the determination can be presented.

As a further example, a list of foodstuff or types of food generally available with textures or texture ranges as required according to the determination can be retrieved from a corresponding database and the result of the retrieval be presented. The types of food may revert to the viscosities or other appropriate rheological properties as discussed herein and/or used in the field, e.g. thin, nectar, honey, etc., and/or may be based on other general language descriptions such as mash, paste, etc. Additionally or alternatively, specific products or product lines may be indicated including, for example, one or more types of menu regularly offered by a hospital, retirement home, etc.

According to various embodiments, the device may provide an indication of the dosage of a thickening agent, for example the thickening agent provided with the kit, required for safe swallowing as determined. For example, a minimum dosage of the thickening agent and/or other or similar agents, may be presented to be added to water or similar fluids for safe swallowing.

The device may be adapted to process an input indicative of a particular texture, food, food type, product, dosage of a thickening agent, etc., which may be selected from a display menu, and to respond to the input by indicating whether a safe swallowing can be expected based on the determinations.

One or more of the above-indicated needs is further satisfied by a replenishment package for replenishment of specific embodiments of the kit outlined above. The kit 100 comprises a thickening agent 106 for thickening a fluid for producing at least one item of foodstuff 118 or 120 with a defined texture for intake by a subject, wherein the thickening agent 106 is provided in form of one or more unit portions 206. The unit portions 206 are adapted for achieving one or more different specific textures when combining the thickening agent 106 with a fluid. The replenishment package may be provided with specific sizes as required for a hospital, retirement's home, stationary or mobile medical practice. Small packages for home use may also be contemplated.

One or more of the above-indicated needs is still further satisfied by another replenishment package 210 for replenishment of specific embodiments of the kit outlined above. The kit comprises a thickening agent 106 for thickening a fluid for producing at least one item of foodstuff with a defined texture for intake by a subject.

Combinations of the above-outlined replenishment packages can also be envisaged.

One or more of the above-indicated needs are satisfied by the use of a thickening agent for determining a swallowing deficiency. The thickening agent is to be used within a framework wherein at least one sensor is provided to be positioned externally or internally on a throat of the subject, to detect throat vibrations associated with an intake of the foodstuff by a subject, and to provide a sensor signal indicative of the detected throat vibrations. The thickening agent is provided for thickening a fluid for producing at least one item of foodstuff with a defined texture for intake by the subject. A device 108 is provided to accept from the sensor a sensor signal associated with the intake of the item of foodstuff by the subject, determine an indication related to a swallowing deficiency based on the sensor signal, and provide an output indicative of a result of the determination.

For intended use, the thickening agent may for example specifically be provided in form of one or more unit portions, wherein a unit portion can be adapted for achieving a defined texture when combining the unit portion of thickening agent with the fluid. The thickening agent may also be portioned into two or more different unit portions; for example, a first unit portion may be provided to produce a first foodstuff item with a first texture, and the second unit portion may be provided to produce a second foodstuff item with a second texture.

One or more of the above-indicated needs is satisfied by the use of a device 108 for determining a swallowing deficiency. The tool is to be used within a framework wherein at least one sensor is provided to be positioned externally or internally on a throat of the subject, to detect throat vibrations associated with an intake of the foodstuff by a subject, and to provide a sensor signal indicative of the detected throat vibrations. A thickening agent is provided for thickening a fluid for producing at least one item of foodstuff with a defined texture for intake by the subject. The device 108 is provided to accept from the sensor a sensor signal associated with the intake of the item of foodstuff by the subject, determine an indication related to a swallowing deficiency based on the sensor signal, and provide an output indicative of a result of the determination.

According to one embodiment, a device may be used as it is conventionally used for water swallow tests. Within the above framework, the tool may be used for measuring at least one intake of a foodstuff item with a texture different from that of water or similar liquid. Additionally or alternatively, the tool may be used for multiple intakes with different textures performed for one subject. For example, the tool could be used for measuring a sequence of intakes of foodstuff items with increasing, or decreasing viscosity values or other appropriate rheological properties. For any of these embodiments, the tool could be used to indicate for each intake the determination of successful or unsuccessful swallowing.

A method for determining a swallowing deficiency is outlined in the following. The method comprises a step of positioning at least one sensor externally or internally on a throat of a subject for detecting throat vibrations associated with an intake of foodstuff by the subject and providing a sensor signal indicative of the detected throat vibrations. The method comprises a further step of producing an item of foodstuff with a defined texture by thickening a fluid with a thickening agent. The method can comprise providing water. The method further comprises a step of providing the item of foodstuff for intake to the subject. The method comprises a step of accepting, by a device, from the sensor a sensor signal associated with the intake of the item of foodstuff by the subject. The method further comprises a step of determining an indication related to a swallowing deficiency based on the sensor signal. The method comprises a further step of providing an output indicative of a result of the determination.

Producing the foodstuff item may comprise combining a fluid such as water with a prescribed portion of the thickening agent by mixing, stirring, etc. or simply providing water.

The method may be performed for a first foodstuff item with a first texture and a second foodstuff item with a second texture, the first texture being different from the second texture. According to various embodiments, both the first and second items of foodstuff may be produced by thickening at least one fluid with the thickening agent. For example, a first dosage of the thickening agent may be used for thickening water to achieve the first foodstuff item with a first texture, and a second dosage of the thickening agent may be used for thickening water to achieve the second foodstuff item with a second texture. Additionally or alternatively to water, other fluid with viscosity in a thin range, or fluid with viscosity in other range may be used.

According to various embodiments, the thickening agent is provided or providable in unit portions. For example, the agent may be provided in packaged form as described above and elsewhere herein, or may be portioned using a spoon or other receptacle, which may or may not comprise a graduation for volume, weight, etc. At least one specific texture can be achieved by combining one or more of the unit portions of the thickening agent with the fluid. According to a simple example, three different textures may be achieved by providing one and the same unit of fluid and adding one, two or three spoons of agent.

According to various embodiments it is intended that multiple intakes are provided to the subject wherein the textures of the corresponding plurality of foodstuff items differ each in viscosity. Then part of the method steps may be performed repeatedly for each of the items. For example, various foodstuff items may be provided to the subject, wherein each item has a higher, or lower, viscosity than the preceding item. According to other embodiments, for example following a nested grid approach, higher or lower viscosities are provided in alternating fashion to determine an individual's threshold viscosity which separates successful from unsuccessful swallowing.

Some of the embodiments with repeated intake of items (with differing textures) by the subject may further comprise that the repetitions are terminated when the device indicates a swallowing deficiency. For example, a sequence of items starting with solid consistency or high viscosity and repeated with items of decreasing viscosity may be stopped when the tool indicates a swallowing difficulty, or at least does no longer indicate a successful swallowing, even if no difficulties are determined by other measures, e.g. visual inspection.

Performing the sequence from thick to thin and stopping as soon as a deficiency is determined or detected may be preferable when the risk of aspiration is to be avoided for an individual. In other cases, the method may repeatedly be performed starting from an item with thin viscosity, e.g., water, and continuing with items of increasingly higher viscosity. The repetition may only be stopped when the tool and other indications consistently indicate the absence of swallowing difficulties.

In general, increasing viscosity tends to decrease the risk of aspiration i.e. increases swallowing safety. However, increasing viscosity also tends to increase risk of residue (i.e. decreases swallowing efficiency). In case of conflicting requirements, safety dominates over efficiency.

According to various embodiments of the invention for determining swallowing deficiencies and/or providing support for diagnosing dysphagia, a subject may swallow multiple foodstuff items with differing textures. A tool is provided for measuring the swallowing activity in response to the different textures. Swallowing deficiencies are determined by automatic analysis of the measurements and the analysis results can be presented.

Generally, assessing the characteristics of the swallowing process, or assessing the risk of aspiration or determination of swallowing deficiencies requires a sequence of increasingly specific diagnostic measurements to be taken, which may also be stressful for the subjects to be diagnosed. According to embodiments of the invention, at least for some subjects or groups of subjects a complex chain of diagnostic measures can be replaced by a simple yet specific diagnosis which can be performed with less stress for the subject, less effort for the medical personnel, in shorter time and/or less costly. For example, cases can be contemplated for which complex endoscopic and/or videofluoroscopic diagnostic can be omitted.

The device may support a specific diagnosis including a recommendation of food textures to be preferred for intake. Vice versa, to the best of the inventor's knowledge there is no approach existing so far wherein appropriate foodstuff rheologies such as nectar, honey, pudding can be recommended from a tool-based detection and analysis of swallowing activity, as opposed to the imaging approaches discussed further above. According to embodiments of the invention, a computer-based tool conventionally employed as a screening tool, e.g. when supporting a water swallow test, can be employed as a diagnostic tool.

According to the inventive approach, a known screening tool for supporting an unspecific diagnosis on the presence or absence of dysphagia may be used for supporting a more specific diagnosis with minor or even without modifications. According to other embodiments, the device may be adapted for implementing the invention and may further be optimized for supporting a more specific determination of swallowing difficulties and/or a diagnosis of dysphagia. In any case, for implementing the invention, an existing computer-based device for analyzing swallowing activities may find a broader field of application than before. On the other hand, basic functions of the device comprising the sensor, and the interworking of both are already implemented, error-proven, and known to the medical personnel. Also for these reasons, the invention may be implemented efficiently and can be integrated into existing medical practice and processes in a hospital, doctor's practice, etc. with little effort.

Known thickening agents may be used for the invention. This eases implementing the invention, for example, in case well-known properties of thickeners can be referred to for shipping and storing inventive kits. Vice versa, known thickening agents with required properties can be selected for a kit.

As another example, medical personnel, e.g., in rehab hospitals may already be used to a particular thickener, or the use of thickeners in general, which can also contribute to efficient implementation of the invention.

Kits may be provided which include a thickening agent as may be preferred for use in a subsequent therapy, easing the step from diagnosis to therapy. This is, however, not a prerequisite for implementing embodiments of the invention.

A dry thickening agent may be used for implementing the invention, e.g., as a constituent for an inventive kit, which provides for an easy handling for shipping, storing and application as compared to diagnostic approaches requiring, for example, specific fluidic components not readily available at an examination site. For the invention, only water, or similar fluidic material is required. It is also noted that the foodstuff items to be swallowed according to the inventive approach do not require any radiating component, as no imaging is intended or required, which further eases handling as compared to, e.g., a diagnostic approach relying on the irradiation of opaque foodstuff such as barium cookies. For example, for the distribution or delivery of inventive kits no regulations with regard to radiation have to be observed.

Generally, a kit according to embodiments of the invention may not require specific handling, as it may contain only dry components. Namely, besides sensor and processing unit (if included), a kit may essentially contain a thickening agent, which may generally be provided in dry form such as in the form of a powder. The same holds true for a replenishment package according to the invention.

It is noted that a kit according to the invention, specifically one or more of the sensor, the thickening agent, and the device, can be flexibly used, i.e. can easily be adapted to various determination/diagnostic conditions or requirements. For example, no new or additional sensor equipment is required according to embodiments of the invention over that used currently for supplementing the water swallow test. As another example, a container with thickening agent included in a kit may be used for preparing one foodstuff item for examining a first subject, or two items for examining a second subject, or any number of foodstuff items as desired for a particular examination. As still another example, the device may be applied for analyzing one or more different textures. Any adaptation to other or further textures, or implementation of new or additional analysis routines may, for example, be efficiently performed based on a software update.

While embodiments of the invention provide support for a specific diagnosis of dysphagia including recommended texture or textures, no complex imaging tools are required and embodiments of the invention can therefore find broad applicability, for example due to its relatively low costs, small size of the kit, etc. For example, the kit may be used as a portable tool for determining swallowing deficiencies and/or diagnosing dysphagia. In this respect, as a specific diagnosis based on the invention does not necessarily require visiting a hospital or doctor's site, the invention allows avoiding discomfort for subjects with respect to moving to such sites, but also with respect to avoiding endoscopic examinations, etc. The screening may be given in various channels of care including the office of a general practitioner.

Use of embodiments of the invention can be contemplated particularly advantageous for specific target groups, for example immobile, disabled, and/or handicapped subjects. Additionally or alternatively, use of embodiments of the invention may be contemplated for subject groups for which it is clear that swallowing deficiencies are present, for example in case of cancer, accident, or neurological impairment such as dementia. In these and other cases, the invention may particularly contribute to the specific diagnosis of which foodstuff to be recommended for the patient.

As an example, it can be contemplated to specifically adapt the computer-based tool according to the invention to recommend particular food or food types as may be provided by, e.g. a rehab hospital or retirement home.

BRIEF DESCRIPTION OF THE DRAWINGS

The invention will further be described in the following with reference to exemplary embodiments illustrated in the figures, in which:

FIG. 1 illustrates a kit 100 for determining a swallowing deficiency according to an embodiment of the invention and its application to a subject 102. The kit 100 comprises a sensor 104, a thickening agent TA in a container 106, and a computing device 108. The device contains a processing unit 140 which computes the information provided by the sensor and outputs a signal.

Figure 1:
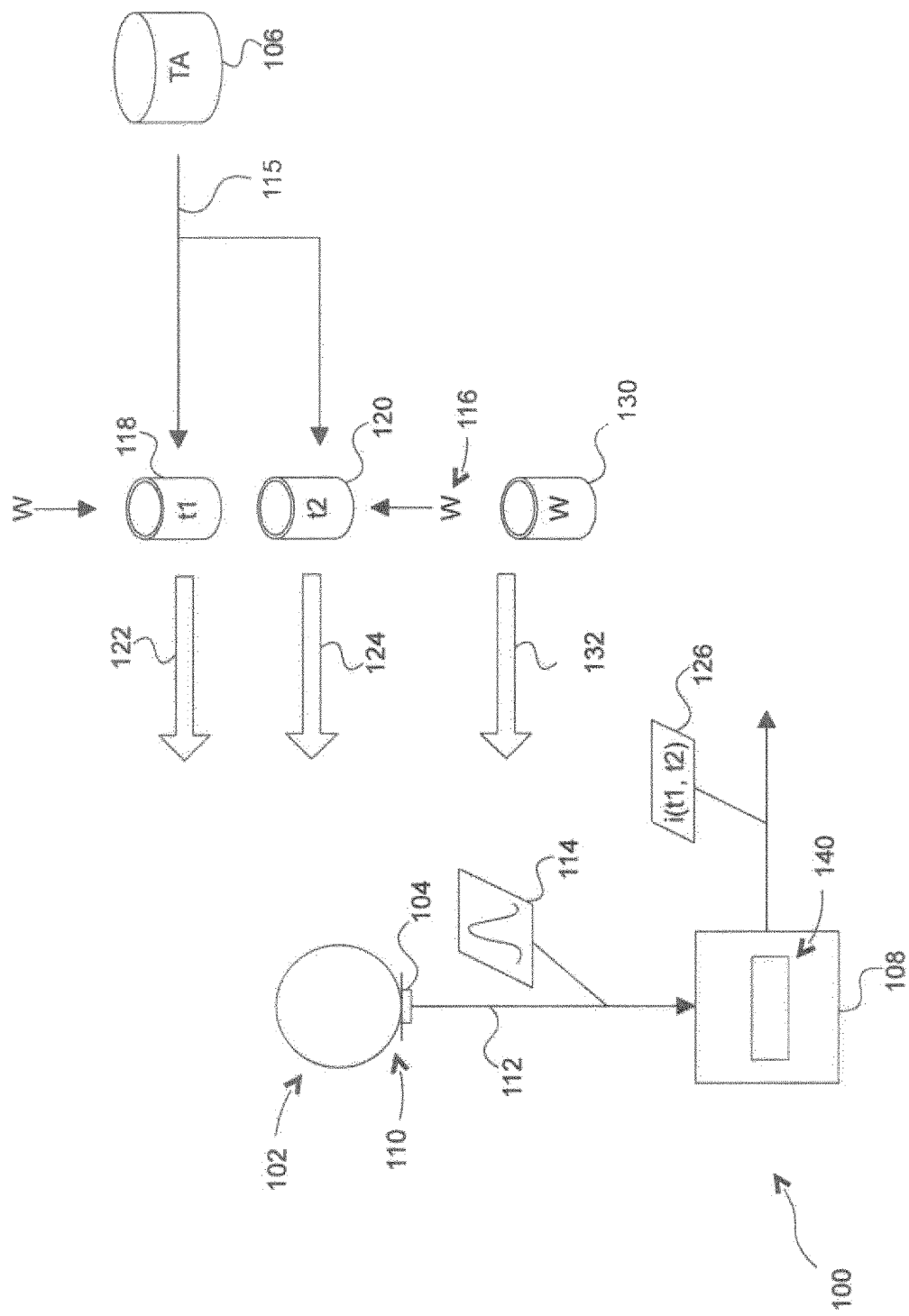
FIG. 1 schematically illustrates a kit according to an embodiment of the invention.

For performing an examination, the sensor 104 may be positioned externally or internally on a throat 110 of subject 102. Sensor 104 may comprise an accelerometer and/or other means for detecting throat 110 vibrations associated with an intake of foodstuff by subject 102. Sensor 104 is shown in FIG. 1 as being connected via wire 112 to device 108 to provide a sensor signal 114 indicative of the detected throat vibrations to device 108. The wire 112 can be replaced by a wireless device between 108 and sensor 104.

Thickening agent TA is schematically illustrated by arrows 115 in FIG. 1 as contributing to thickening a fluid 116, which may be water "W" or other fluid, for producing two items 118, 120 of foodstuff with a specific texture t1 and t2, respectively. Water 130 can also be provided to the subject. As indicated by arrows 122, 124, and 132 items 118, 130 and 120 are intended for intake by subject 102.

Device 108 accepts the sensor signals 114 associated with the intake of the foodstuff items 118, 120, 130 respectively. Based on signal or signals 114, device 108 operates to determine an indication related to the characteristics of the swallowing process, the assessing of the risk of aspiration or a swallowing deficiency of subject 102. An output 126 indicative of a result of the determination is provided. According to one embodiment, an indication of at least one of the textures t1, W and t2 may selectively be output depending on whether or not at least one swallowing deficiency has been determined with regard to one or both of the textures.

The general environment depicted in FIG. 1 will further be referred to herein below for discussing various aspects and further exemplary embodiments of the invention.

Figure 2:
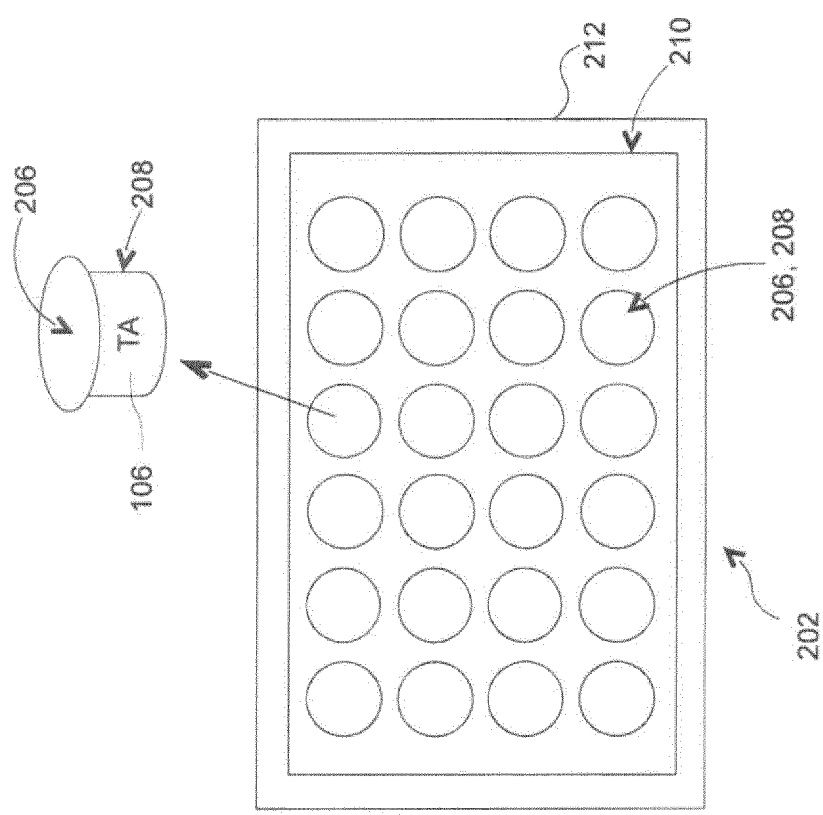
FIG. 2 illustrates a packaging of a thickening agent and additional dry foodstuff items as components of a kit according to an embodiment of the invention.

FIG. 2 illustrates a specific exemplary packaging 202 for the thickening agent TA, and further comprises a packaging 212. Generally, the ensemble 202 may represent part of a kit similar to kit 100 of FIG. 1, or may represent at least a part of a replenishment package for replenishing or refilling a kit, for example a kit for which the thickening agent and/or solid foodstuff items have been used up.

For reasons of clarity and conciseness it is assumed that one and the same thickening agent TA is used in the kits, i.e. the same thickening agent TA may be constituent of kit 100 and ensemble 202. However, it is noted that according to other embodiments a kit may comprise more than one thickener and that different kits may comprise different thickening agents, depending on the specifics of any particular kit application.

Further, it is noted that the thickening agent TA may be provided differently packaged in different kits. For example, the container 106 depicted in FIG. 1 may comprise loose or bulky TA in powder form without further sub-packaging. A dosing of loose TA may be achieved using a spoon, a graduated cup or glass, or other measuring receptacle. In addition, the TA may be given in stick packs of premeasured powder.

According to the example depicted in FIG. 2, the thickening agent TA is provided, e.g., delivered, in form of a plurality of unit portions 206, wherein each unit portion 206 is packaged in a separate jar, container, or receptacle 208. A plurality of receptacles 208 is stored in a blister 210. A plurality of blisters 210 may be received in an outer package 212.

The receptacle 208 may seal the unit portion 206 of TA contained inside and may be, for example, of a generally cylindrical form as illustrated in FIG. 2 or may have any other form which appears suitable for appropriately storing or applying the plurality of containers 208. According to other embodiments, unit portions (or any other portioning of the TA) may be provided in form of capsules, cells, pads, etc., which may be collected loosely inside an outer package, or which may be packaged with a further, intermediate level of packaging similar to the packaging in blisters as illustrated in FIG. 2 or other, e.g., loose intermediate packages.

While ensemble 202 includes thickening agent TA, other kits or replenishment packages may only contain one or more thickening agents. Packages for replenishment only containing solid foodstuff items for refill of used solid items of a kit can also be contemplated.

It is to be understood that a kit or replenishment package may generally be provided to examine a plurality of subjects. Amount of thickening agent and/or solid foodstuff items included in a kit may be selected according to intended size of the kit/replenishment package, e.g. for stationary/non-stationary use, storage life for the thickening agent and/or the solid foodstuff items versus number of subjects expected to be diagnosed per time, etc. As a simple example, a kit may be provided with sufficient thickening agent to examine 100 subjects, wherein each examination may comprise intake of a foodstuff item of texture nectar, honey, and pudding. Assuming the texture nectar requires 1 spoon of agent, honey requires 2 spoons of agent, and pudding requires 3 spoons of agent, each spoon weighing 5 gram of agent, a container with 3 kilogram of thickening agent would be required to be included in the kit.

Figure 3:
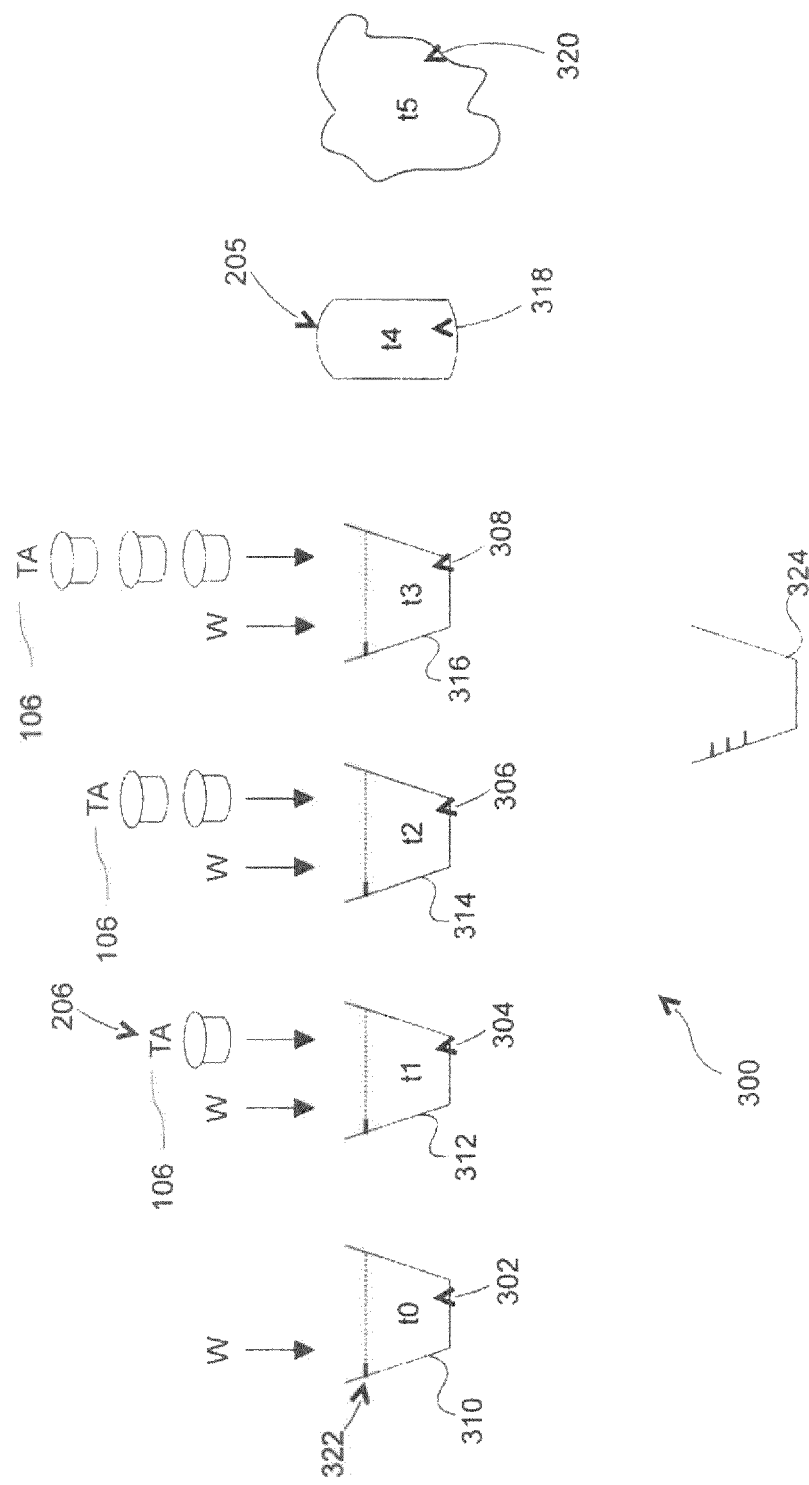
FIG. 3 illustrates a plurality of foodstuff items with differing textures prepared for intake according to an embodiment of the invention.

FIG. 3 illustrates an example of a set 300 of foodstuff items prepared for intake by a subject to be examined for swallowing deficiencies. The set comprises fluidic foodstuff items 302, 304, 306, and 308 schematically depicted in drinking vessels 310, 312, 314, 316 as well as solid foodstuff items 318, 320.

Foodstuff item 302 is assumed to contain 100 ml of pure water "W" having a texture t0 represented by a viscosity of around 1-4 mPa s. Item 302 may be produced by appropriately filling vessel 310 with drinking water, mineral water, tea, etc. Accordingly, letter "W" is intended to refer besides water to any fluid with preferably comparable viscosity such as tea, coffee, soup. Vessels 310-316 are illustrated with a graduation 322 indicating a desired filling level.

Foodstuff item 304 may be produced by filling one unit portion 206 of thickening agent TA into vessel 312 and filling up the vessel 312 with water to reach level 322. Due to one unit portion of TA being included, the water is thickened to reach a nectar-type viscosity t1 which may be, for example, about 300 mPa s.

Foodstuff item 306 may be produced by filling two unit portions 206 of thickening agent TA into vessel 314 and filling up the vessel 314 with water until level indication 322 is reached. Due to two unit portions of TA being included, the water is thickened to reach a honey-type viscosity t2 which may be, for example, be about 1500 mPa s.

Foodstuff item 308 may be produced by filling three unit portions 206 of thickening agent TA into vessel 316 and filling up the vessel 316 with water until level indication 322 is reached. Due to three unit portions of TA being included, the water is thickened to reach a pudding-type viscosity t3 which may, for example, be about 5000 mPa s. Solid t4 foodstuff item 318 may comprise one biscuit 205 as discussed with reference to FIG. 3. No preparation may be required for intake except for removing any packaging around item 318. Foodstuff item 320 may be of solid, but crushy consistency t5, and may be produced by crushing one of the biscuits 205 of FIG. 2.

While the example in FIG. 3 indicates thickening agent portioned such that 1, 2 and 3 unit portions 206, respectively, are required for three different textures, various other dosages can be contemplated. For example, unit portions may be provided to achieve three specific textures by adding 2, 3 and 4 unit portions to a fluid, or 1, 3 and 5 portions, etc. Various combinations can be contemplated for efficiently producing two, three or more different textures from one thickening agent only.

Instead of using only one thickening agent, two or more different agents may be provided with a kit or replenishment package. For example, a first thickening agent may be used to produce textures such as nectar, a second agent may be used to produce honey, and a third texture may be used to produce pudding. Alternatively, when a single thickening agent is provided, three different packages with three different portion volumes may be provided, the first package containing the amount of agent required for texture nectar, the second containing the amount of agent required for texture honey, and the third containing the amount of agent required for texture pudding.

Although four vessels 310-316 are shown in FIG. 3, subject examination may be performed using fewer vessels. For example, a single vessel only may be used to sequentially produce one, two or more foodstuff items and/or provide the foodstuff item/s for intake. A number of vessels as required may be included in a kit and/or a replenishment package according to the invention.

At least one graduated receptacle 324 may be provided with a kit and/or replenishment package. One or more of these receptacles may be used for one or more of measuring the fluids indicated with "W" in FIG. 3 to prepare the fluidic foodstuff items, and/or for measuring thickening agent, for example in case the agent is provided in loose or bulky form and/or in case a desired dosage cannot be achieved by simply adding one or more unit portions.

It is noted that a kit according to the invention may include further components such as an instruction manual, for example for the sensor, the software/hardware tool for analyzing the sensor signals, and/or for the thickening agent. Further, information on medical guidelines, download information for software updates, etc. may be provided. In this respect it is again highlighted that according to some embodiments the computer-based tool is implemented on a server or similar facility to be reached via a network such as a hospital network or intranet, the Internet, etc. The kit handed out to the user or examiner may therefore comprise a network address, e.g. an intranet or Internet address to be entered into a web browser or similar tool which may then provide for a user interface for using for network-based computing resources. According to an exemplary embodiment, a kit may comprise only the sensor and a cable such as an USB cable for connection with a general purpose computer as measuring/computing "hardware", besides the thickening agent, other foodstuff items, etc.

With reference to the flow diagram of FIG. 4, an application of a kit for examining a subject, i.e. for determining 400 a swallowing deficiency, will be described according to an embodiment of the invention. For purposes of discussion, kit 100 and modifications thereof will be referred to as illustrated in the previous figures.

In step 402, sensor 104 of kit 100 is positioned externally or internally on throat 110 of subject 102. In step 404, an item of foodstuff with a specific texture is produced by thickening a fluid with a thickening agent or water is provided without the addition of a thickening agent. This step may refer, for example, to a production of foodstuff item 304 illustrated in FIG. 3, wherein thickening agent TA is added to water in vessel 312 to achieve a defined texture t1. The step may additionally or alternatively refer to production of any of items 306 and 308 with textures t2 and t3, respectively.

In step 403, the patient is asked to hum or make a deliberate noise such as coughing. The signal from this action is compared by the device to a library of "good" signals as opposed to "bad" signals. In the case of a "good" signal, the flow diagram continues to the next step. In the case of a "bad" signal, indicating that the sensor 104 is positioned incorrectly on the patient throat, the examiner is prompted to repositioned the sensor correctly and the flow recommences at step 402.

In step 404 one or more items of foodstuff 118 is/are prepared as explained above.

In step 406, the produced foodstuff item 304 is provided for intake to the subject 102. Sensor 104 detects the throat vibrations associated with the intake of foodstuff item 304. Sensor signal 114 indicative of the detected throat vibrations is provided to device 108. Accordingly, with step 408 the tool 108 accepts the sensor signal 114.

In step 410, device 108 operates to determine an indication related the assessment of the swallowing process in a subject or to a swallowing deficiency based on the sensor signal 114. In step 412, the device 108 provides output 126 which is indicative of a result of the determination. In step 416 the examination may end by providing a recommendation as a support for a diagnosis, wherein the recommendation may relate to a recommended minimum texture, texture range, viscosity, foodstuff, etc.

The steps 404-412 may be repeated for multiple foodstuff items, as indicated by arrow 414. Specifically, an examination may comprise multiple intakes of foodstuff items with a similar texture, for example for verifying a significance of a detection or for other statistical reasons. Additionally or alternatively, an examination may comprise multiple intakes of foodstuff items with differing texture. For example, an examination may comprise the intake of a sequence formed from the six items illustrated in FIG. 3. Consequently, various embodiments of an examination may comprise six repetitions of steps 404-412. The corresponding production of any item immediately before intake allows performing the various intakes and measurements at different times, which may, for example, be preferred to minimize stress for the subject.

Figure 4:
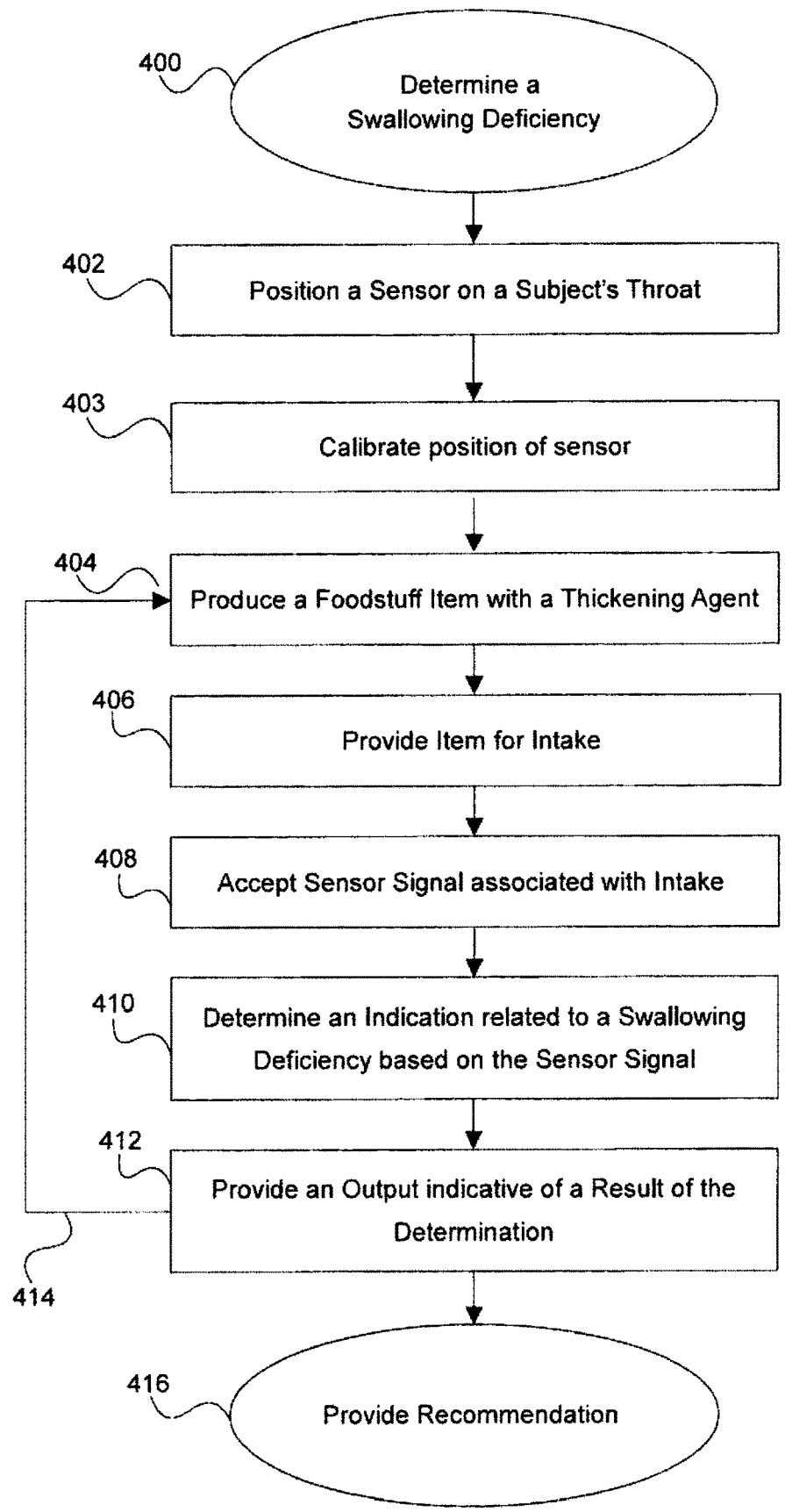
FIG. 4 is a flow diagram illustrating an examination according to an embodiment of the invention.

In addition, the entire process described in FIG. 4 might be repeated with a different subject.

Referring further to the exemplary set of items depicted in FIG. 3, and with specific regard to the repetition of production step 404, the various repetitions aim at producing, amongst others, the foodstuff items 304, 306, 308 from thickening water with the appropriate amount of thickening agent TA. Specifically, the agent TA may be provided in unit portions 206 as illustrated in FIG. 2, and the specific textures t1, t2 and t3 are achieved by combining an appropriate number of TA unit portions 206 with water. Other items such as items 302, 318, 320 may be produced without adding thickening agent.

According to a modified embodiment, an examination may deviate from what is indicated by arrow 414 in FIG. 4, and some or all of the items desired for intake may collectively be produced prior to providing one after the other to the subject for intake and measurement. The process depicted in FIG. 4 may for example be modified in that step 404 would be performed in parallel for at least a subset of foodstuff items and the steps 406-412 would then be repeated according to at least the number of items prepared.

With regard to repeatedly performing step 406, the various foodstuff items with, e.g., differing texture may be provided at random or according to a particular sequence for intake by the subject. The items may for example be sorted according to texture. Referring again to the exemplary foodstuff items illustrated in FIG. 3, a sequence according to increasing, or decreasing texture or viscosity may be formed. Following the sequence of items in FIG. 3 from left to right, the subject may first intake water, then the water item 302 with thin viscosity t0, and may then intake items 304, 306 and 308 with nectar t1, honey t2, and pudding t3 viscosity, respectively, and may continue with solid t4 item 318 and crumbly t5 item 320. Vice versa, the subject may start with intake of solid 318 or crumbly item 320 to continue with items 308, 306, 304 and 302 with viscosities decreasing from t5 or t4 to t0. Any other sequence may be envisaged, each measurement being independent.

The repeated provision of foodstuff items according to one of the sequences described above may be terminated when one or more termination conditions are met. For example, providing a sequence of items with decreasing viscosity to the subject may be terminated when the examiner determines by physical inspection that there is a swallowing deficiency. As an additional or alternative condition, the computer-based tool 108 may indicate a swallowing deficiency, which may lead to termination of the examination even if no deficiency has been detected by physical inspection, and vice versa. A recommendation issued in step 416 may then be based on the last texture or viscosity which was swallowed without any deficiency determined.

Similarly, a sequence continuing from low to high viscosity may be terminated when the first texture or viscosity has been determined to have been swallowed without deficiency or/and with the required swallowing efficiency.

Modifications may comprise, with reference to the exemplary sequence formed from the items indicated in FIG. 3 from left to right, starting with nectar t1 viscosity instead of with water t0, for example if it is generally known that a swallowing deficiency is present. If it is determined (step 410) that a swallowing deficiency is present with nectar, the examination may be continued with honey t2. If it is determined (repeated step 410) that a swallowing deficiency is present with honey, the examination is continued with pudding t3, etc.

Additionally or alternatively, a sequence of intakes may comprise alternating textures, for example in order to determine a limit for a recommended viscosity for a subject with a minimum number of intakes.

Figure 5:
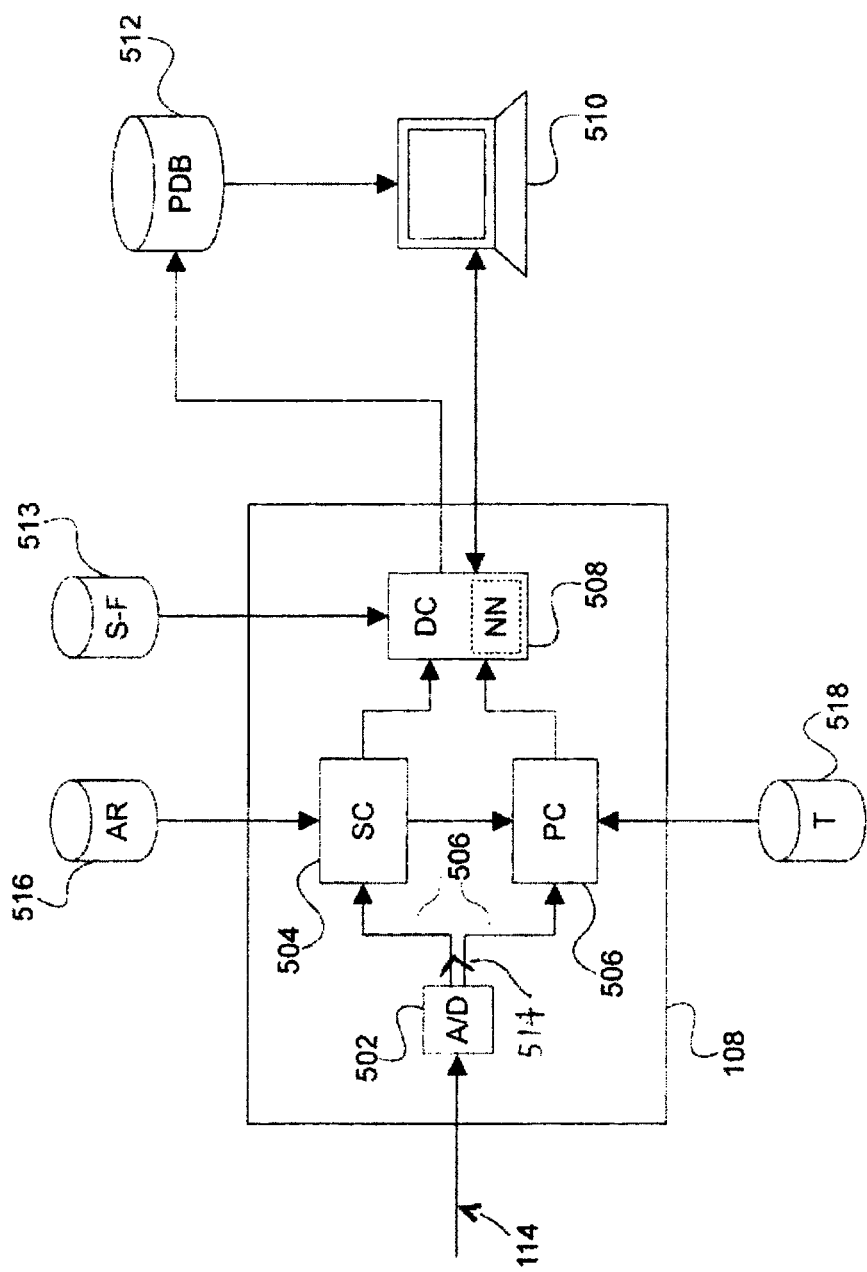
FIG. 5 illustrates functional components of a computing device according to an embodiment of the invention.

In case it is intended to terminate an examination as soon as a recommended texture has been determined, instead of preparing all or any foodstuff items in advance, it may be preferable to prepare any specific foodstuff item only after it is clear from the previously performed intakes that the item is actually required for further intake and analysis. FIG. 5 illustrates functional components of the computing device 108 of FIG. 1 according to an embodiment. Generally, the device 108 may be implemented by a computing hardware such as a stationary or portable computing device which may be situated locally at an examination site. Additionally or alternatively, the device 108 may comprise remote computing hardware which may be adapted to perform, for example, part or all of the determination step 410 illustrated in FIG. 4, while a hardware at the examination site is provided for accepting the sensor signal (step 408) and presenting an output (steps 412 and/or 416).

Various software or firmware may be executed on the device 108 to implement the required functionality. However, the following discussion will focus on functional aspects for sake of conciseness and therefore further details on hardware/software implementations will mostly be omitted.

The computing device 108 comprises a component A/D 502 for accepting the sensor signal 114 depicted in FIG. 1. A stochastic component SC 504 and a profile component PC 506 are provided for analyzing signal representations as described in more detail below. A determination component DC 508 is adapted for determining an indication related to a swallowing deficiency based on the analysis of sensor signal 114 as provided from one or both of components 504 and 506. The computing device 108 may provide an output representing a result of the determination on a console 510 and/or to a database 512.

From a general point of view, sensor signals can be contemplated which clearly represent either a successful swallowing, or a risk of aspiration. However, in many cases the presence or absence of a swallowing deficiency may not be unambiguously imprinted on the signal, i.e. the signal may show some ambiguities. In order to be able to nevertheless arrive at a conclusion, one approach may comprise to independently analyze, in a first stage, various aspects of the sensor signal and appropriately combining the separate analysis results, in a second stage, to arrive at a final result as reliable as possible. The first stage is exemplarily illustrated by components 504 and 506 in FIG. 5, the second stage is illustrated with component 508.

An operation in more detail of the computing device 108 as depicted in FIGS. 1 and 5 will be discussed with reference to the flow diagram of FIG. 6. Generally, the operation 600 is related to determining a swallowing deficiency based on a signal such as signal 114.

In step 601, the patient is asked to hum or make a deliberate noise such as coughing. The signal from this action is compared by the device to a library of "good" signals as opposed to "bad" signals. In the case of a "good" signal, the flow diagram continues to the next step. In the case of a "bad" signal, indicating that the sensor 104 is positioned incorrectly on the patient throat, the examiner is prompted to repositioned the sensor correctly and the flow recommences at step 601.

In step 602, the device 108 accepts an input, for example via console 510. The input may, for example, indicate the foodstuff item next to be provided to the subject, or an item which recently has been provided to the subject. Based on such input, the device 108 may define and store in a storage component S-F 513 (FIG. 5) data representing an association of a particular signal 114, or a portion and/or other aspects thereof, to a foodstuff item or related property such as a texture thereof. Instead of a particular item, the input indication may relate to a foodstuff, foodstuff class, a particular product, or to a texture, e.g., an indication of a viscosity or viscosity range such as 'nectar', 'honey', 'pudding', etc.

An input indication may relate to a particular intake, or to a sequence of intakes. For example, an input indication may relate to a sequence of intakes with increasing, or decreasing viscosities. The tool 108 may then retrieve information on textures supposed for any particular intake of the sequence from predefined data.

The user, e.g. an examiner, may enter the input indication or indications of step 602 for example by appropriately selecting foodstuff items, a sequence to be performed, etc. from a menu presented to him or her via the console 510. As another example, the user may acknowledge a particular foodstuff item, texture, and/or sequence of intakes offered to him or her on a display of console 510, and may then proceed as presented to him or her in response to the selection.

In step 604, which may coincide with step 408 of FIG. 4, component 502 accepts from sensor 108 the sensor signal 114 associated with the intake of an item of foodstuff by subject 102. The component 502 may receive the signal 114 from sensor 104 (push), and/or may actively control sensor 104 which may include retrieving the signal (pull) therefrom. Depending on the details of the implementation, component 502 may comprise modules for signal processing such as, for example, an A/D-converter, in order that a digital signal 514 is provided for analysis to one or both of components 504 and 506.

In step 606, one or both of components 504 and 506 operate to perform various analysis of signal 514. If both components are present and active in device 108, they may operate in parallel and/or sequentially, as indicated by the arrows in FIG. 5. Stochastic component 504 may analyze signal 514 for stochastic or statistical properties. For example, parameters such as stationarity, normality, and/or a dispersion ratio may be determined. Details on stochastic analysis of sensor signals can be found in U.S. '177 and will therefore not be discussed in any detail here. One or more analysis routines AR may be predefined and provided in an associated storage 516 for access by component 504.

Additionally or alternatively, component 506 may operate to compare parts, portions or aspects of signal 516 with predefined templates T stored in an associated database 518.

The templates may, for example, represent signal aspects which may be defined as characteristic for one or more types of swallowing deficiencies, dysfunctions or difficulties. The aspects represented in database 518 may relate to statistical signal properties such as those analyzed by component 504. Therefore, component 506 may make use of results of component 504 when comparing, for example parameter values of characterizing parameters to predefined values or value ranges as stored in database 518.

According to some embodiments, one or more of the templates stored in database 518 may be applicable for specific textures or texture ranges only. For example, the database 518 may comprise sets of templates, wherein each set is applicable for a given texture range, e.g. viscosity range, etc. As a specific example, in case swallowing of a nectar-type foodstuff item is to be analyzed, a different set of templates may be accessed or retrieved from database 518 than in the case of analyzing a honey-type foodstuff item, a pudding-type foodstuff item, etc.

At least one of steps 606 and 608 may coincide with step 410 in FIG. 4. In step 608, an indication related to a swallowing deficiency is determined. The determination component 508 may accept analysis results from one or both of components 504 and 506 and may determine therefrom an indication of the presence or not of at least one swallowing difficulty based on the sensor signal 114. For example, the component 508 may operate to combine various analysis results provided by components 504 and 506 into one determination result.

As a specific example, component 508 may comprise a neural network NN to arrive at a decision based on the analysis results provided by components 504 and 506, i.e. to generate a determination. The neural network may be trained to generate, in response to the various analysis results being input, an output which may comprise a probability value indicating a probability for the absence or presence of at least one swallowing difficulty. More sophisticated embodiments can be contemplated which reveal multiple probability values each representing the probability for the presence or absence of a specific type of swallowing difficulty in the analyzed signal. Different from an unspecific diagnosis representing merely the presence or absence of a swallowing deficiency per se, according to embodiments of the present invention the presence of absence of a swallowing difficulty can be determined for each of one or more different textures, and thereby a range of textures recommended for safe swallowing can be determined.

With regard to analysis of sensor signals and determination of swallowing deficiencies based thereupon, it is noted that embodiments of a computing device may operate as described in detail U.S. '177. The signal analysis described therein may be applicable to swallowing water in a conventional water swallow test and may likewise be applicable to swallowing foodstuff items with textures different from water, as described herein.

According to some embodiments, the analysis may be adapted to specific textures or limited texture ranges according to theoretical and/or mathematical considerations regarding throat vibrations in response to swallowing different textures. Additionally or alternatively, signal analysis may be adapted to specific texture ranges based on expert's knowledge, experiments, etc. For example, analysis results may be adapted to coincide with results of physical monitoring of swallowing activities.

Still further, "expert's knowledge" may also be implemented in the form of artificial intelligence, e.g. by providing an expert system or by accordingly training a neural network depicted with letters "NN" in FIG. 5. For example, a neural network trained for determining swallowing deficiencies based on a conventional water swallow test may be copied and the copies may be trained further, each for a specific, separate texture range. For example, one neural network each may be provided for analyzing swallowing deficiencies in a viscosity range of thin, nectar, honey, pudding. According to another embodiment there may be different algorithms for water, nectar, honey and pudding.

According to some embodiments, the determination component 508 may be adapted to calculate a new texture based on the textures of the foodstuff items actually provided for intake to the subject. For example, in case a first texture has been swallowed without difficulties, and a second, neighboring texture revealed the presence of difficulties, the component 508 may determine a third texture in between the first and second texture, and may output the calculated third texture with a request or hint to the examiner related to a recommendation for testing the calculated third texture, for example in order to maximize or otherwise optimize a range of textures, viscosities, foodstuff, etc. available for the subject.

In step 610, which may coincide to step 412 of FIG. 4, the device 108 provides an output indicative of a result of the determination in step 608. For example, the component 508 may retrieve from storage 513 information associated with the currently analyzed signal or signal portion, wherein the information may comprise a texture, foodstuff item, etc. as may have been stored in step 602 to be associated with the presently analyzed signal. An indication of the presence or absence of a swallowing deficiency may then be presented in conjunction with the retrieved information via console 510 to the examiner. In addition, the information may be stored in the patient's database PDB 512 for later reference by medical or nursing personnel, for example in case a swallowing deficiency has in fact been determined. The database 512 may be queried, for example, for particular foodstuff, products, etc., and may, based on the stored analysis results, return whether the queried item would be recommendable or not.

Specifically, the device may output an indication of a swallowing deficiency present such as "ASPIRATION !" (swallowing safety) and/or "RESIDUE" (swallowing efficiency) and may additionally output the texture or texture range, for which that determination result is valid. Additionally or alternatively, the device 108 may be adapted to provide for an output which is indicative of a result without findings, i.e. an output "NORMAL SWALLOWING" plus an indication of a texture range, and/or foodstuff class such as nectar, honey, pudding, etc., which has been determined to not cause swallowing deficiency.

As indicated by arrow 612, steps 604 to 610 may be repeated for different textures, i.e. the number of foodstuff items desired for intake. According to step 614, device 108 may provide for an output at the end of the examination which may comprise a summary of the determinations of the prior repetitions. In step 616, the determination routine 600 returns control to a higher level of device 108.

Figure 6:
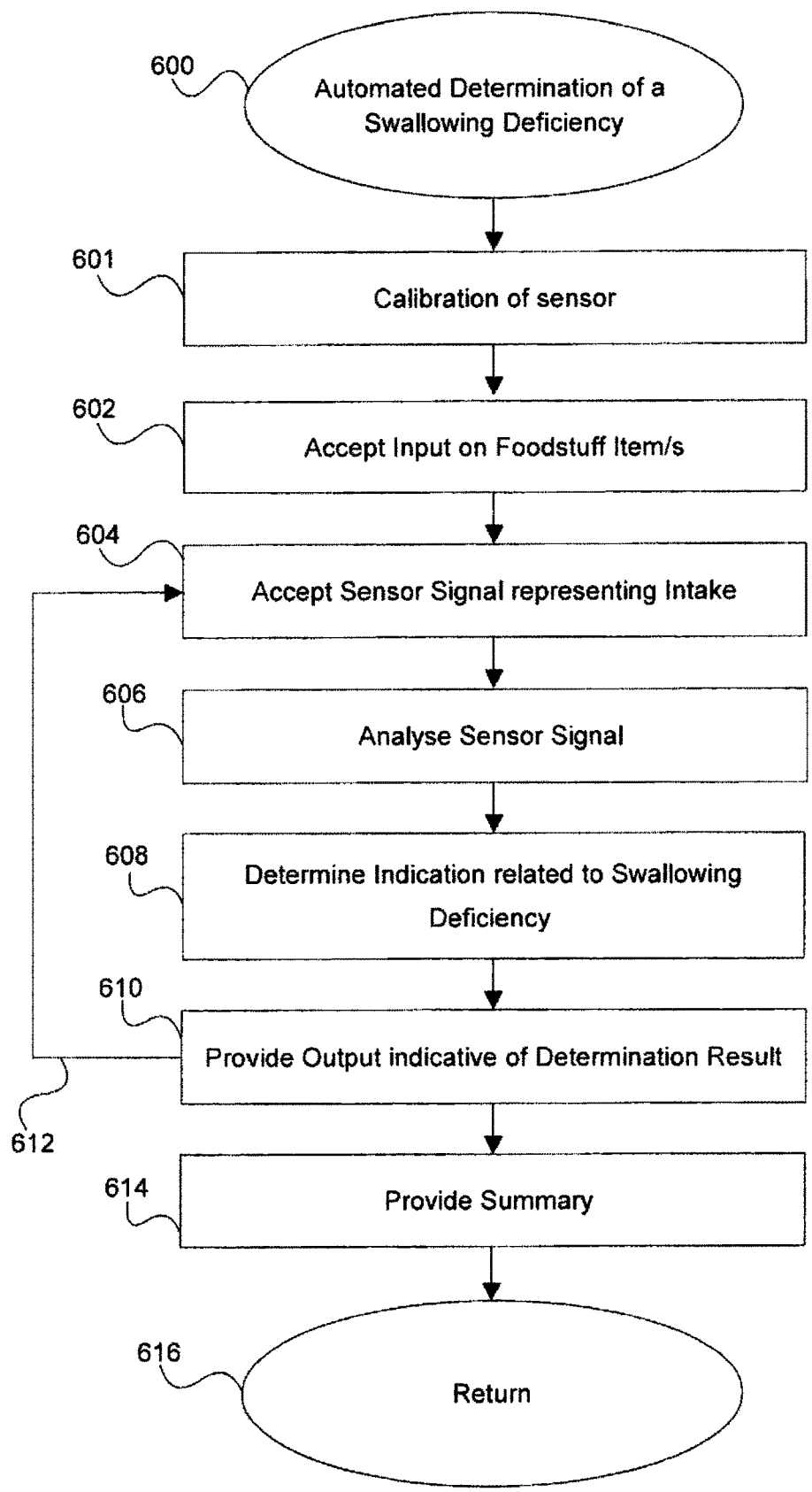
FIG. 6 is a flow diagram illustrating an operation of the device of FIG. 5.

Various modifications of the operation depicted in FIG. 6 can be contemplated. For example, various steps shown in (repeated) sequence in FIG. 6 may be performed in different order, in parallel, and/or may be performed several times. As but one specific example, the input step 602 may be performed repeatedly, e.g. prior to each intake of foodstuff to set device 108 ready for signal reception and enable clear distinction between signal portions representing intake of different foodstuff items/textures and artifacts not related to the subject's swallowing. As another example, step 601 may be repeated if calibration is deemed to have failed.

As another example, the intermediate output of analysis results for single foodstuff items in step 610 may be omitted, or minimized by, e.g., merely indicating successful signal reception, and a comprehensive output including a texture range for successful swallowing may only be performed in the final output step 614. Deferring output of results to final step 614 may for example waive the necessity of foodstuff intake in a strict sequence of, for example, increasing or decreasing viscosity. Moreover, such configuration would enable more complex analysis computations which may, for example, refer to combinations of sensor signals representing different foodstuff items and/or textures, or which include comparing properties or aspects of signals representing different foodstuff items and/or textures.

While tool 108 is depicted in FIG. 5 as comprising two analysis components 504 and 506, according to another embodiment only one component is provided. For example, only the stochastic component 504 may be present to provide parameter values for one, two, or more statistically determined properties of input signals to the neural network NN of component 508.

While the invention has been described in relation to various presently preferred embodiments, it is to be understood that this description is intended non-limiting and for illustrative purposes only. In particular, various combinations of features wherein the features have been described separately hereinbefore are apparent as advantageous or appropriate to the skilled artisan. Vice versa, various fully elaborated embodiments have been described hereinbefore; however, other embodiments can be contemplated according to which the invention is realized with lesser constituents, components, steps, or other features. Accordingly, it is intended that the invention be limited only by the scope of the claims appended hereto.

The following numbered examples provide for further illustration of various aspects of the invention.

Example 1

A method for determining a swallowing deficiency, comprising:
positioning at least one sensor internally or externally on a throat of a subject for detecting throat vibrations associated with an intake of foodstuff by the subject and providing a sensor signal indicative of the detected throat vibrations;
producing an item of foodstuff with a defined texture by thickening a fluid with a thickening agent or water;
providing the item of foodstuff for intake to the subject, accepting, by a computer-based tool, from the sensor a sensor signal associated with the intake of the item of foodstuff by the subject, determining an indication related to a swallowing deficiency based on the sensor signal, and providing an output indicative of a result of the determination.

Example 2

As example 1, and
wherein the method is performed for a first foodstuff item with a first texture and a second foodstuff item with a second texture, the first texture being different from the second texture.

Example 3

As example 2, and
wherein both the first and second items of foodstuff are produced by thickening at least one fluid with the thickening agent.

Example 4

As example 1, and
wherein the thickening agent is provided or providable in unit portions and at least one defined texture is achieved by combining one or more of the unit portions of the thickening agent with the fluid.

Example 5

As example 2, and
wherein the textures of a plurality of foodstuff items differ in viscosity and the method is repeatedly performed by providing foodstuff items with increasing viscosity, or decreasing viscosity or other order viscosity to the subject.

Example 6

As example 5, and
wherein the repeated provision of foodstuff items with different texture to the subject is terminated when the computer-based tool indicates a swallowing deficiency.

Example 7

Study Protocol for Training the Processing Unit

The purpose of this study is to explore the utility of swallowing accelerometry classifiers to detect impaired swallowing in adult subjects at risk for oropharyngeal dysphagia of non-congenital, non-surgical, and non-oncologic origin.

The primary objective is to collect swallowing accelerometry signals for the purpose of building classifiers to detect impaired swallowing in adult subjects at risk of oropharyngeal dysphagia of non-congenital, non-surgical, and non-oncologic origin.

The secondary objective is to evaluate the impact of sip volume and bolus rheology on accelerometry based classifiers.

Study Endpoint:
The study endpoint is supervised training error rates for accelerometry based classifiers to discriminate impaired swallowing on boluses of different rheology.

Study Population:
Adult subjects at risk for oropharyngeal dysphagia of non-congenital, non-surgical, and non-oncologic origin will be evaluated for enrollment regardless of whether they are suspected of having dysphagia. Subjects must also belong to at least one of the following groups: stroke, acquired brain injury, or registered as a patient for other reasons not covered by the exclusion criteria and over the age of 65. Approximately 200 patients are enrolled in the trial.

Device
Swallowing accelerometry is the study of swallowing vibrations measured using a sensor placed on the neck. The sensor includes a dual-axis swallowing accelerometer, embedded in a plastic molded sensor housing, which attaches to the neck using a square of double sided adhesive tape. This non-invasive method for detecting aspiration has shown potential promise for clinical assessment applications. The lower and upper cutoff frequencies of the bandpass filter are set at 0.1 Hz and 3 kHz, respectively. Both signal channels are sampled at 10 kHz.

After the data is collected and sent to the Core Lab, a series of processing steps are used to filter out artifacts such as those attributable to the signal acquisition system, head movements vocalizations, etc. The swallowing events are identified from within the filtered signals. Both anterior-posterior and superior-inferior axis accelerometry signal features will be extracted in multiple domains (time, frequency, and time-frequency) and analyzed to identify the most discriminating features that could be used to characterize the swallowing events.

Gold Reference Standard
Videofluoroscopic Swallowing Study (VFSS). A videofluoroscopic swallowing study is an x-ray study of oropharyngeal swallowing function. Moving x-ray images are taken of the mouth and throat while food and liquid, mixed with barium, is swallowed. VFSS using a standardized protocol is considered the current gold-standard instrumental assessment for swallowing.

Study Design:
This study is a prospective exploration of swallowing accelerometry signals, collected during water swallows, and during swallows of barium-stimuli of different rheology, time-synchronized with VFSS in subjects at risk for oropharyngeal dysphagia of non-congenital, non-surgical, and non-oncologic origin.

Eligible subjects will swallow up to 6 discrete sips of water during which accelerometry signals will be recorded. Immediately following the water sips, subjects will undergo VFSS using up to 6 sips of thin barium contrast agent, and up to 3 boluses each of barium thickened to three different consistencies using Thicken Up Clear (TUC), a xanthan gum-containing powder thickener (Nestlé Health Science):

mildly-thick (1.2 g of TUC/100 ml), moderately-thick (2.4 g of TUC/100 ml), and extremely-thick (3.6 g of TUC/100 ml). Note: The actual TUC doses used are reduced appropriately to compensate for the added viscosity due to the addition of barium. The resulting viscosity closely matches the viscosity obtained when the reported doses of TUC are mixed with water alone. Swallows of the barium stimuli will be simultaneously recorded using accelerometry and VFSS.

Water, thin liquid barium, and mildly-thick barium sips will be taken either from a single 6 oz cup (containing ~4 oz of fluid) or as single sips from a series of 6 oz cups (each containing ~4 oz of fluid). Approximately half of the enrolled subjects will use each method (single versus series of cups). Moderately-thick and extremely-thick barium will be taken by spoon. In all cases, sip volume will be measured by cup weights after each sip or spoonful.

The invention claimed is:

1. A method for training a processing unit for assessing characteristics of a swallowing process in a subject, the method comprising:
   providing a kit comprising at least one device comprising the processing unit and a sensor capable of detecting throat vibrations externally or internally on a throat of the subject, the kit further comprising a thickening agent formulated for thickening a fluid for producing at least one item of foodstuff with a defined texture for intake by the subject, the processing unit after the training is capable of outputting an indication of the characteristics of the swallowing process in the subject,
   wherein the processing unit is configured to accept a sensor signal associated with an intake of an item of tagged foodstuff by the subject, wherein the processing unit accepts the sensor signal by a process comprising the steps of:
   a) performing at least once the following steps:
      i) providing to the subject at least three items of tagged foodstuff for oral intake, each of the at least three items of tagged foodstuff selected from the group consisting of water, a foodstuff item with a texture having a nectar-type viscosity of 51 mPa s to 350 mPa s, a foodstuff item having a honey-type viscosity of 301 mPa s to 1750 mPa s, and a foodstuff item having a pudding-type viscosity of more than 1750 mPa s,
      ii) assessing the characteristics of the swallowing process in the subject resulting from the intake of the at least three items of tagged foodstuff by the subject with video fluoroscopy; and
      iii) using the results of step i) and ii) for training the processing unit, the training comprising determining the sensor signal resulting from the throat vibrations resulting from the intake of at least two items of tagged foodstuff by the subject, and forwarding the sensor signal to the processing unit, the processing unit is operated by a computer executable software, and the computer executable software provides an assessment of the characteristics of the swallowing process, and the assessment from the computer executable software results from correlating the sensor signal with the assessment resulting from the video fluoroscopy,
      repeating steps i) to iii) at least once to improve correlation between an assessment of the characteristics of the swallowing process of the subject resulting from the sensor signal and the assessment of the characteristics of the swallowing process resulting from the video fluoroscopy, wherein the subject is selected from the group consisting of the same subject and a different subject; and
   b) thereby obtaining a trained processing unit,
   wherein the method comprises at least one step selected from the group consisting of (A) implementing a neural network and (B) determining parameters of the computer executable software running on and instructing the trained processing unit.

2. The method of claim 1, wherein step iii) comprises:
   a) providing the trained processing unit;
   b) performing the method defined in step a) on the trained processing unit on a group of 10 to 30 subjects;
   c) thereby obtaining a further trained processing unit; and
   d) resubmitting the further trained processing unit to steps b)-d) for 1-30 times.

3. The method of claim 1, further comprising a step c) wherein the trained processing unit is validated in a validation phase.

4. The method of claim 3, comprising a further step of validating that the trained processing unit provides the same assessment of the characteristics of the swallowing process of the subject as the video fluoroscopy by comparing the indication of a swallowing deficiency output by the video fluoroscopy and output by the trained processing unit,
   and thereby obtaining a trained and validated processing unit.

5. The method of claim 1, wherein the trained processing unit is configured for at least one of (i) outputting an indication of a swallowing deficiency or (ii) assessing a risk of aspiration comprising at least one operation selected from the group consisting of assessing swallowing safety and assessing swallowing efficiency.

6. The method according to claim 1 wherein the steps i)-iii) are performed at least twice, each with one food stuff item selected from the group consisting of water, a foodstuff item with a texture having a nectar-type viscosity, a foodstuff item having a honey-type viscosity, and a foodstuff item having a pudding-type viscosity; and the method comprises associating the performing of each step i) with the one specific foodstuff item thereby providing a sequence of foodstuff items that is to be provided to the subject in step a) or using different algorithms for each of water, a foodstuff item with a texture having a nectar-type viscosity, a foodstuff item having a honey-type viscosity, and a foodstuff item having a pudding-type viscosity.

7. The method of claim 6 wherein, in the sequence of foodstuff items to be provided, at least two of the foodstuff items are the same.

8. The method of claim 1, wherein, within each sequence of foodstuffs to be provided to the subject, none of the foodstuffs are provided to the subject twice.

9. The method of claim 1, wherein one of the at least three foodstuffs of step i) in step a) is water.

10. The method of 1, wherein a sequence of the at least three foodstuff items is water, a foodstuff item with a texture having a nectar-type viscosity, a foodstuff item having a honey-type viscosity, and a foodstuff item having a pudding-type viscosity, and wherein the water is first in the sequence of the at least three foodstuff items.

11. A kit comprising:
   a processing unit configured for assessing characteristics of a swallowing process in a subject;
   a sensor capable of detecting throat vibrations, the sensor adapted to detect vibrations externally or internally on a throat of the subject; and a thickening agent formulated for thickening a fluid for producing at least one item of foodstuff with a defined texture for intake by the subject,
wherein the processing unit after training is capable of outputting an indication of the characteristics of the swallowing process in the subject, and
wherein the processing unit is capable of accepting from the sensor a sensor signal associated with the intake of an item of tagged foodstuff by the subject, the processing unit configured to:
a) perform at least once the following steps:
   i) provide to the subject at least three items of tagged foodstuff for oral intake, each of the at least three items of tagged foodstuff are selected from the group consisting of water, a foodstuff item with a texture having a nectar-type viscosity of 51 mPa s to 350 mPa s, a foodstuff item having a honey-type viscosity of 301 mPa s to 1750 mPa s, and a foodstuff item having a pudding-type viscosity of more than 1750 mPa s,
   ii) assess the characteristics of the swallowing process in the subject resulting from the intake of at least two items of tagged foodstuff by the subject with video fluoroscopy; and iii) train the processing unit using the results of step i) and ii), the training comprising determining the sensor signal resulting from the throat vibrations resulting from the intake of at least two items of tagged foodstuff by the subject, and forwarding the sensor signal to the processing unit, the processing unit is operated by a computer executable software, and the computer executable software provides an assessment of the characteristics of the swallowing process, and the assessment from the computer executable software results from correlating the sensor signal with the assessment resulting from the video fluoroscopy,
   repeating steps i) to iii) at least once to improve correlation between an assessment of the characteristics of the swallowing process of the subject resulting from the sensor signal and the assessment of the characteristics of the swallowing process resulting from the video fluoroscopy, wherein the subject is selected from the group consisting of the same subject and a different subject; and
b) thereby obtaining a trained processing unit,
and the processing unit is configured to perform at least one step selected from the group consisting of (A) implementing a neural network and (B) determining parameters of the computer executable software running on and instructing the trained processing unit.

12. A method for assessing characteristics of swallowing in a subject, the method comprising assessing swallowing safety and/or-swallowing efficiency, the assessing comprising the steps:
a) providing to a subject at least three items of foodstuff for oral intake,
b) assessing the characteristics of the swallowing in the subject associated with the oral intake of the at least three items of foodstuff with a kit comprising at least one device comprising a processing unit and a sensor capable of detecting throat vibrations, the kit further comprising a thickening agent for thickening a fluid for producing at least one item of foodstuff with a defined texture for intake by the subject, the processing unit is supplied with a sensor signal from the sensor, the sensor adapted to detect the throat vibrations of the subject externally or internally,
wherein the processing unit after training is capable of outputting an indication of the characteristics of the swallowing process in the subject, and
wherein the processing unit is capable of accepting from the sensor the sensor signal, the sensor signal is associated with the oral intake of the item of tagged foodstuff by the subject, the method comprising:
performing at least once the following steps:
   i) providing to the subject at least three items of tagged foodstuff for the oral intake, each of the at least three items of tagged foodstuff are selected from the group consisting of water, a foodstuff item with a texture having a nectar-type viscosity of 51 mPa s to 350 mPa s, a foodstuff item having a honey-type viscosity of 301 mPa s to 1750 mPa s, and a foodstuff item having a pudding-type viscosity of more than 1750 mPa s,
   ii) assessing the characteristics of the swallowing process in the subject resulting from the oral intake of at least two items of tagged foodstuff by the subject with video fluoroscopy; and
using the results of step i) and ii) for the training of the processing unit, the training comprising determining the sensor signal resulting from the throat vibrations resulting from the intake of at least two items of tagged foodstuff by the subject, and forwarding the sensor signal to the processing unit, the processing unit is operated by a computer executable software, and the computer executable software provides an assessment of the characteristics of the swallowing process, and the assessment from the computer executable software results from correlating the sensor signal with the assessment resulting from the video fluoroscopy,
   repeating steps i) to iii) at least once to improve correlation between an assessment of the characteristics of the swallowing process of the subject resulting from the sensor signal and the assessment of the characteristics of the swallowing process resulting from the video fluoroscopy, wherein the subject is selected from the group consisting of the same subject and a different subject; and
thereby obtaining a trained processing unit,
wherein the method comprises at least one step selected from the group consisting of (A) implementing a neural network and (B) determining parameters of the computer executable software running on and instructing the trained processing unit.

13. The method of claim 12, wherein at least one of the at least three different defined items of tagged foodstuffs is water.

14. The method of claim 12 wherein the subject is provided with an additional item of tagged foodstuff that has a different texture than the at least three items of foodstuff previously used.

15. The method of claim 12, wherein a first item of the at least three items of tagged foodstuff provided in step a) is water.

* * * * *